United States Patent
Shafer et al.

(10) Patent No.: US 9,580,494 B2
(45) Date of Patent: *Feb. 28, 2017

(54) METHODS AND DEVICE TO NEUTRALIZE SOLUBLE TOXIC AGENTS IN THE BRAIN

(71) Applicant: Medtronic, Inc., Minneapolis, MN (US)

(72) Inventors: Lisa Lynn Shafer, Stillwater, MN (US); Deepak Ramesh Thakker, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/719,795

(22) Filed: May 22, 2015

(65) Prior Publication Data

US 2016/0152695 A1 Jun. 2, 2016

Related U.S. Application Data

(63) Continuation of application No. 12/120,269, filed on May 14, 2008, now Pat. No. 9,040,045.

(60) Provisional application No. 60/984,775, filed on Nov. 2, 2007, provisional application No. 60/917,911, filed on May 14, 2007.

(51) Int. Cl.
C07K 16/18 (2006.01)
A61K 39/00 (2006.01)

(52) U.S. Cl.
CPC ........ *C07K 16/18* (2013.01); *A61K 2039/505* (2013.01); *A61K 2039/54* (2013.01); *A61K 2039/545* (2013.01); *C07K 2317/54* (2013.01)

(58) Field of Classification Search
None
See application file for complete search history.

(56) References Cited

U.S. PATENT DOCUMENTS

| | | |
|---|---|---|
| 7,090,661 B2 | 8/2006 | Morris et al. |
| 2002/0102261 A1 | 8/2002 | Raso |
| 2003/0165496 A1 | 9/2003 | Basi et al. |
| 2005/0090648 A1 | 4/2005 | Tsurushita et al. |
| 2007/0166311 A1 | 7/2007 | Greferath et al. |
| 2008/0292625 A1 | 11/2008 | Schroeter et al. |
| 2009/0117120 A1 | 5/2009 | Grimm et al. |
| 2009/0142270 A1 | 6/2009 | Schroeter et al. |

FOREIGN PATENT DOCUMENTS

| | | |
|---|---|---|
| WO | WO 98/44955 A1 | 10/1998 |
| WO | WO 2004/032868 A2 | 4/2004 |

OTHER PUBLICATIONS

Yin 2002 "Amyloid .beta. induces smac release via AP-1/Bim activation in cerebral endothelial cells" J Neurosci 22(22):9764-9770.*
PCT Patent Application No. PCT/US2008/063559, filed May 14, 2008; International Search Report issued Aug. 12, 2008.
Bacskai, et al., "Imaging of amyloid-beta deposits in brains of living mice permits direct observation of clearance of plaques with immunotherapy" 2001, *Nat Med* 7(3):369-372.
Bacskai, et al., "Multiple Mechanisms are Involved in Clearance of Amyloid-Beta by Immuntherapy" 2001, *Society for Neuroscience Abstracts*, vol. 27, No. 2.
Bacskai, et al., "Non-Fc-mediated mechanisms are involved in clearance of amyloid-beta in vivo by immunotherapy" 2002, *J Neurosci* 22(18):7873-7878.
Banks, et al., "Passage of amyloid beta protein antibody across the blood-brain barrier in a mouse model of Alzheimer's disease" 2002, *Peptides* 23(12):2223-2226.
Banks, et al., "Effects of a behaviorally active antibody on the brain uptake and clearance of amyloid beta proteins," 2005, *Peptides*, 26:287-294.
Bard, et al., "Peripherally administered antibodies against amyloid beta-peptide enter the central nervous system and reduce pathology in a mouse model of Alzheimer disease" 2000, *Nat Med* 6(8):916-919.
Bard, et al., "Epitope and isotype specificities of antibodies to beta -amyloid peptide for protection against Alzheimer's disease-like neuropathology" 2003, *Proc Natl Acad Sci U S A* 100(4):2023-2028.
Billings, et al., "Intraneuronal Abeta causes the onset of early Alzheimer's disease-related cognitive deficits in transgenic mice" 2005, *Neuron* 45(5):675-688.
Bowers, et al., "Amyloid immunotherapy-engendered CNS inflammation." 2002, *Neurobiol Aging* 23(5):675-676; discussion 683-684.
Callahan, et al., "Augmented senile plaque load in aged female beta-amyloid precursor protein-transgenic mice" 2001, *Am J Pathol* 158(3): 1173-1177.
Carty, et al., "Intracranial administration of deglycosylated C-terminal-specfici anti-AB antibody efficiently clears amyloid piques without activating microglia in amyloid-depositing transgenic mice" 2006, *J Neuroinflammation*, 3:11.
Chauhan, et al., "Distribution of intraventricularly administered antiamyloid-beta peptide (Abeta) antibody in the mouse brain" 2001, *J Neurosci Res* 66(2):231-235.

(Continued)

*Primary Examiner* — Adam M Weidner
(74) *Attorney, Agent, or Firm* — Mueting, Raasch & Gebhardt, P.A.

(57) ABSTRACT

Methods, agents and devices for treating a patient to reduce accumulation of certain proteins in the brain are described. Such proteins include amyloid beta (Aβ), and the methods, agents and devices are useful for reducing the accumulation of Aβ, which is a principal constituent of the plaques associated with such diseases as Alzheimer's disease (AD). Antibodies to Aβ, when delivered systemically or directly into the central nervous system, improve cognitive deficits in a transgenic mouse model of AD. However, unlike peripheral antibodies to Aβ, which increased cerebral vascular plaques and hemorrhages, direct central administration did not result in such an increase cerebral vascular plaques and hemorrhages.

20 Claims, 26 Drawing Sheets

(56) References Cited

OTHER PUBLICATIONS

Chauhan, et al., "Reversal of amyloid beta toxicity in Alzheimer's disease model Tg2576 by intraventricular antiamyloid beta antibody" Jul. 2002, *J Neurosci Res* 69(1):10-23.
Chauhan, et al., "Intracerebroventricular passive immunization with anti-Abeta antibody in Tg2576" Oct. 2003, *J Neurosci Res* 74(1):142-147.
Chauhan, et al. "Effect of age on the duration and extent of amyloid plaque reduction and microglial activation after injection of anti-Abeta antibody into the third ventricle of TgCRND8 mice" 2004, *J Neurosci Res* 78(5):732-741.
Chauhan, et al., "Efficacy of anti-Abeta antibody isotypes used for intracerebroventricular immunization in TgCRND8" Mar. 2005, *Neurosci Lett* 375(3):143-147.
Chauhan, "Intracerebroventricular Passive Immunization with Anti-OligoAbeta Antibody in TgCRND8" Feb. 2007, *Journal of Neuroscience Research*, 85:452-463.
Das, et al., "Amyloid-beta immunization effectively reduces amyloid deposition in FcRgamma–/– knock-out mice" 2003, *J Neurosci* 23(24):8532-8538.
De Strooper, et al., "Proteolytic processing and cell biological functions of the amyloid precursor protein" 2000, *J Cell Sci* 113(Pt 11):1857-1870.
DeMattos, et al., "Peripheral anti-A beta antibody alters CNS and plasma A beta clearance and decreases brain A beta burden in a mouse model of Alzheimer's disease" 2001, *Proc Natl Acad Sci U S A* 98(15):8850-8855.
Dodart, et al., "Immunization reverses memory deficits without reducing brain Abeta burden in Alzheimer's disease model" May 2002, *Nat Neurosci* 5(5): 452-457.
Evin, et al., "Biogenesis and metabolism of Alzheimer's disease Abeta amyloid peptides" 2002, *Peptides* 23(7):1285-1297.
Frosch, et al., "Effect of Passive Immunotherapy on the Rate of Progression of Cerebral Amyloid Angiopathy (CAA) in Transgenic Mice" Apr. 2007, *FASEB Journal*, Abstract only.
Furlan, et al., "Vaccination with amyloid-beta peptide induces autoimmune encephalomyelitis in C57/BL6 mice" 2003, *Brain* 126(Pt 2):285-291.
Gelinas, et al., "Immunotherapy for Alzheimer's disease" 2004, *Proc Natl Acad Sci U S A* 101 Suppl 2:14657-14662.
Gitter et al., "Passive Immunization of APPV717F Transgenic Mice with Mid-Domain—or Amino—Terminal—Reactive Anti-Abetaantibodies Produce Differential Effects on Immunoreactive Abeta Burden and Fibrillar (Thioflavin-S Positive) Plaque Deposits", Society for Neuroscience Abstract Viewer and Itinerary Planner, 33rd Annual Meeting of the Society of the Neuroscience: New Orleans, LA, Nov. 8-12, 2003.
Hale, et al., "Impaired visuospatial recognition memory but normal object novelty detection and relative familiarity judgments in adult mice expressing the APPswe Alzheimer's disease mutation" 2005, *Behav Neurosci* 119(4):884-891.
Hock, et al., "Generation of antibodies specific for beta-amyloid by vaccination of patients with Alzheimer disease" 2002, *Nat Med* 8(11):1270-1275.
Hock, et al., "Antibodies against beta-amyloid slow cognitive decline in Alzheimer's disease" 2003, *Neuron* 38(4):547-554.
Holtzman et al., "A Beta Immunization and Anti-A Beta Antibodies: Potential Therapies for the Prevention and Treatment of Alzheimer's Disease" Dec. 2002, *Advanced Drug Delivery Reviews*, Amsterdam, NL.
Klyubin, et al., "Amyloid beta protein immunotherapy neutralizes Abeta oligomers that disrupt synaptic plasticity in vivo" 2005, *Nat Med* 11(5):556-561.
Kotilinek, et al. "Reversible memory loss in a mouse transgenic model of Alzheimer's disease" 2002, *J Neurosci* 22(15):6331-6335.
Masters, C. L. and K. Beyreuther "Alzheimer's centennial legacy: prospects for rational therapeutic intervention targeting the Abeta amyloid pathway" 2006, *Brain* 129(Pt 11):2823-2839.

Mohajeri et al., "Passive Immunization Against Beta-Amyloid Peptide Protects Central Nervous System (CNS) Neurons from Increased Vulnerability Associated with an Alzheimer's Disease-Causing Mutation," Sep. 2002, *The Journal of Biological Chemistry*, 277:33012-33017.
Morgan, "Mechanisms of a beta plaque clearance following passive A beta immunization" 2005, *Neurodegener Dis* 2(5):261-266.
Nicoll, et al., "Neuropathology of human Alzheimer disease after immunization with amyloid-beta peptide: a case report" 2003, *Nat Med* 9(4):448-452.
Ognibene, et al., "Aspects of spatial memory and behavioral disinhibition in Tg2576 transgenic mice as a model of Alzheimer's disease" 2005, *Behav Brain Res* 156(2):225-232.
Patton, et al., "Amyloid-beta peptide remnants in AN-1792-immunized Alzheimer's disease patients: a biochemical analysis" 2006, *Am J Pathol* 169(3):1048-1063.
Pfeifer, et al. "Cerebral hemorrhage after passive anti-Abeta immunotherapy" 2002, *Science* 298(5597): 1379.
Prada et al., "Antibody-Mediated Clearance of Amyloid-Beta Peptide from Cerebral Amyloid Angiopathy Revealed by Quantitative in Vivo Imaging" Feb. 2007, *The Journal of Neuroscience: The Official Journal of the Society for Neuroscience* 27:1973-1980.
Racke, et al., "Exacerbation of cerebral amyloid angiopathy-associated microhemorrhage in amyloid precursor protein transgenic mice by immunotherapy is dependent on antibody recognition of deposited forms of amyloid beta" 2005, *J Neurosci* 25(3):629-36.
Schenk, et al., "Immunization with amyloid-beta attenuates Alzheimer-disease-like pathology in the PDAPP mouse" 1999, *Nature* 400(6740): 173-177.
Schenk, "Amyloid-beta immunotherapy for Alzheimer's disease: the end of the beginning" 2002, *Nat Rev Neurosci* 3(10):824-828.
Schmidt, et al., "ELISA method for measurement of amyloid-beta levels" 2005, *Methods Mol Biol* 299:279-297.
Solomon, et al. "Disaggregation of Alzheimer beta-amyloid by site-directed mAb" 1997, *Proc Natl Acad Sci U S A* 94(8):4109-4112.
Tamura, et al., "The F(ab)'2 fragment of an Abeta-specific monoclonal antibody reduces Abeta deposits in the brain" 2005, *Neurobiol Dis* 20(2):541-549.
Turnbull, et al., "Intracerebroventricular passive immunization. II. Intracerebroventricular infusion of neuropeptide antisera can inhibit neuropeptide signaling in peripheral tissues" 1998, *Endocrinology* 139(1):128-136.
Vasilevko, et al., "Novel approaches for immunotherapeutic intervention in Alzheimer's disease" 2006, *Neurochem Int* 49(2):113-126.
Webster, et al. "Antibody-mediated phagocytosis of the amyloid beta-peptide in microglia is differentially modulated by C1q" 2001, *J Immunol* 166(12):7496-7503.
Wilcock, et al., "Number of Abeta inoculations in APP+PS1 transgenic mice influences antibody titers, microglial activation, and congophilic plaque levels" 2001, *DNA Cell Biol* 20(11):731-736.
Wilcock, et al., "Intracranially administered anti-Abeta antibodies reduce beta-amyloid deposition by mechanisms both independent of and associated with microglial activation" May 2003, *J Neurosci* 23(9):3745-3751.
Wilcock, et al., "Passive amyloid immunotherapy clears amyloid and transiently activates microglia in a transgenic mouse model of amyloid deposition" 2004, *J Neurosci* 24(27):6144-6151.
Wilcock, et al., "Passive immunotherapy against Abeta in aged APP-transgenic mice reverses cognitive deficits and depletes parenchymal amyloid deposits in spite of increased vascular amyloid and microhemorrhage" 2004, *J Neuroinflammation* 1(1):24.
Wilcock, et al., "Microglial activation facilitates Abeta plaque removal following intracranial anti-Abeta antibody administration" 2004, *Neurobiol Dis* 15(1):11-20.
Wyss-Coray, et al., "TGF-beta1 promotes microglial amyloid-beta clearance and reduces plaque burden in transgenic mice" 2001, *Nat Med* 7(5):612-618.

\* cited by examiner

A. 1 week post-injection

B. 4 weeks post-injection

C. 8 weeks post-injection

A. 5 min scoring:

B. 10 min scoring:

C. 5 min scoring:

D. 10 min scoring:

A. 5 min scoring:

B. 10 min scoring:

A. 1 week post-injection

B. 4 weeks post-injection

C. 8 weeks post-injection

A. Parenchymal Aβ plaque load in cerebral cortex

B. Vascular Aβ plaque load in cerebral cortex

C. Parenchymal Aβ plaque load in hippocampus

A. Parenchymal plaques

B. Vascular plaques

A. Parenchymal plaques

B. Vascular plaques

METHODS AND DEVICE TO NEUTRALIZE SOLUBLE TOXIC AGENTS IN THE BRAIN

RELATED APPLICATIONS

This application is a continuation application of U.S. patent application Ser. No. 12/120,269 filed on May 14, 2008, which will issue as U.S. Pat. No. 9,040,045 on May 26, 2015 and which claims the benefit of Provisional Application No. 60/917,911, filed on May 14, 2007 and Provisional Application No. 60/984,775, filed on Nov. 2, 2007, which provisional applications are hereby incorporated herein in their respective entireties to the extent that they do not conflict with the disclosure presented herein.

FIELD

This disclosure relates to the use of novel brain infusion techniques and to the use of therapeutic agents and delivery devices for treating diseases characterized by aberrant accumulation of toxic soluble proteins. More particularly, this disclosure relates to the administration of therapeutic agents to target amyloid beta accumulations and thereby treat or study diseases associated with beta amyloid accumulation in the brain of a subject.

BACKGROUND

Various approaches have been aimed at the treatment of diseases caused or manifested by enhanced secretion of an otherwise normal protein, production of a pathological soluble or membrane bound protein, or abnormal conformational changes or folding of a peptide or protein in a mammal. Traditional techniques to target such toxic proteins or the aberrant expression of proteins include the administration of small molecules to affect the rate or amount of production of the proteins or antibodies that will specifically bind to proteins of interest and cause them to be cleared from the body.

The administration of therapeutic antibodies or antibody fragments has had drawbacks that limit their applicability in humans, particularly when administered into the blood stream. New techniques such as chimerization and humanization have been developed to reduce the immunogenicity of the antibodies or antibody fragments. Some newly developed antibodies are completely free of epitopes recognized as foreign by the human immune system and may be generated by using transgenic mouse systems or phage/phagemid display. Such completely humanized antibodies are the driving force behind the fast-paced expansion of antibody product pipelines. Problems, such as toxicity, short-half life, and inability of antibody to cross the blood-brain-barrier (BBB), still exist.

Methods and agents that will enhance the neutralization or clearance of certain proteins in the brain and delivery devices to aid in the administration of such agents is desired.

BRIEF SUMMARY

In various embodiments, methods, agents and devices for treating or studying a subject to reduce accumulation of certain proteins in the brain are described. In numerous embodiments, the disclosure presented herein relates to methods and agents useful for reducing the accumulation of a peptide termed β-amyloid or Abeta or Aβ, which is a principal constituent of the plaques associated with such diseases as Alzheimer's disease (AD). Embodiments of the disclosure include the targeted delivery of agents to the subject's central nervous system (CNS) that inhibit the production of Aβ, decrease the accumulation of Aβ, or increase the clearance of Aβ.

In some embodiments, antibodies against various regions of Aβ peptide are used to reduce levels of cerebral Aβ.

Various embodiments of the disclosure describe systems. Such a system includes a catheter for delivering an antibody to a targeted region. The catheter is coupled to an infusion device configured to deliver the antibody through the catheter. The system may further include a sensor. The sensor may detect an attribute of the nervous system, which attribute may reflect pathology associated with a disease or the amount of antibody present in the targeted region. The system may further include a microprocessor. The microprocessor may analyze output from the sensor and regulate the amount of antibody delivered to the brain or other target site.

Many embodiments of the disclosure describe methods for treating or studying a neurological disease in a subject. Such a method includes delivering an antibody directly to a region of the subject's CNS, such as a region of the brain or intrathecal space of the spinal cord, through an implanted catheter. The catheter is implanted in the CNS so that a discharge portion lies in or adjacent to a predetermined infusion site of the brain, such as the parenchyma, the intraventricular space, the subdural space or the subarachnoid space; or spinal cord. An amount of the antibody effective to treat or study the disease is delivered through the catheter. The catheter may be coupled to an implantable infusion device. The infusion device may be an implantable pump system as described herein or any known or future developed implantable pump system. In some embodiments, an external pump system or a port is coupled to the catheter. The external pump or port may be used for trialing a subject prior to placing an implantable pump or in subjects where the implantable pump is not suitable. The external pump system or port maybe used temporarily or permanently to treat a patient.

Various embodiments provide methods for treating or studying diseases associated with cerebral vascular amyloid plaques or clearing of some or all cerebral vascular amyloid plaques. Such a method includes chronically delivering to the CNS of a subject an anti-Aβ antibody in an amount effective to treat a patient with such plaques, study the effects of the antibody on the plaques, or to clear the plaques.

Various embodiments methods, systems, devices, or compositions described herein provide one or more advantages over known methods and apparatuses using antibodies to treat neurological disorders. For example, use of an implantable infusion device and implantable catheter to deliver an antibody directly to a targeted CNS region allows for greater antigenic specificity and reduced systemic side effects, such as complement binding and initiating an unintended immune response, unintentional reactivity, or cytotoxicity towards human tissues distinct from the intended target. Further, housing an antibody in an infusion device will extend the half-life of the antibody, as the infusion device will shield the antibody from self-recognition as foreign, enhancing bioavailability at its intended target. In addition, use of an infusion device to deliver an antibody may allow for programmable infusion, allowing for temporally specific therapy windows. These and other advantages will be evident to one of skill in the art upon reading the disclosure herein.

Figure 1:
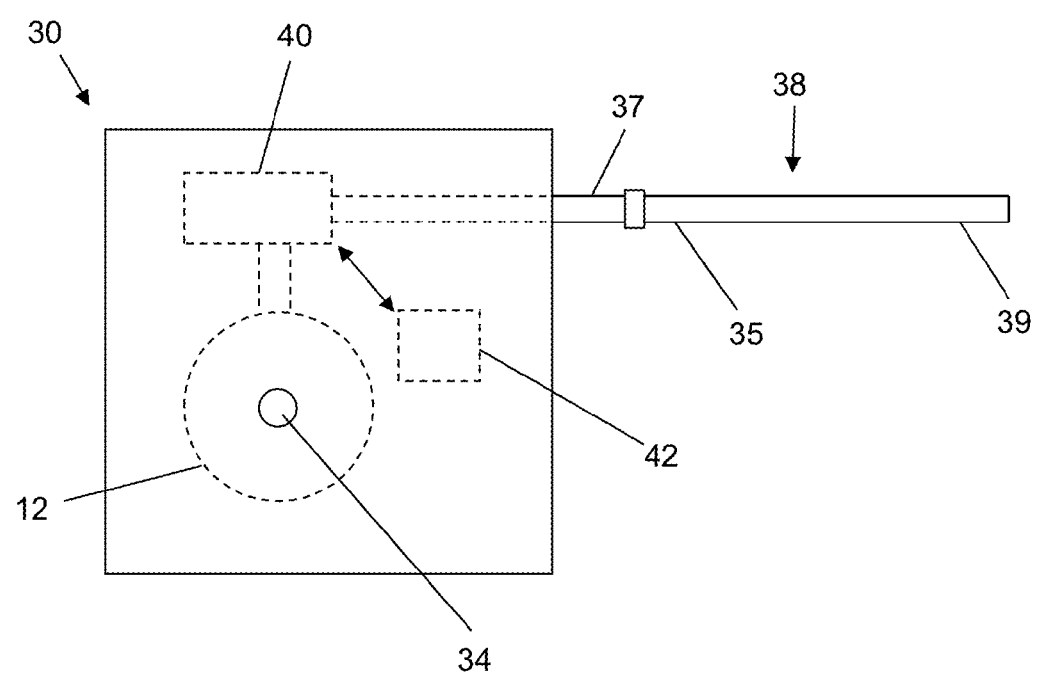
FIG. 1 is a drawing of a schematic side view of a representative infusion device.

For all bar graphs *=$P<0.05$; =$P<0.01$; and *=$P<0.001$.

The drawings are not necessarily to scale. Like numbers used in the figures refer to like components, steps and the like. However, it will be understood that the use of a number to refer to a component in a given figure is not necessarily intended to limit the component in another figure labeled with the same number. In addition, the use of different numbers to refer to components is not necessarily intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

DEFINITIONS

All scientific and technical terms used herein have meanings commonly used in the art unless otherwise specified. The definitions provided herein are to facilitate understanding of certain terms used frequently herein and are not meant to limit the scope of the present disclosure.

As used herein, the singular forms "a", "an", and "the" encompass embodiments having plural referents, unless the content clearly dictates otherwise. As used herein, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

As used herein, the terms "treat" or the like means alleviating, slowing the progression, preventing, attenuating, or curing the treated disease.

As used herein, "disease", "disorder", "condition" or the like, as they relate to a subject's health, are used interchangeably and have meanings ascribed to each and all of such terms.

As used herein, "subject" means a mammal to which an agent, such as an antibody, is administered for the purposes of treatment or investigation. Mammals include mice, rats, cats, guinea pigs, hamsters, dogs, sheep, monkeys, chimpanzees, and humans.

Amyloid Beta

In various embodiments, compositions as described herein include an antibody directed to amyloid beta. As used herein, "beta amyloid", "amyloid beta", "Abeta" and "Aβ" are used interchangeably. Aβ is peptide of about 39-43 amino acids that corresponds to a peptide formed in vivo upon cleavage of an amyloid beta precursor protein (APP or ABPP) by beta-secretase (at the N-terminal portion of Aβ) and gamma secretase (at the C-terminal portion of Aβ). See, e.g., Strooper and Annaert (2000; *J. Cell Sci.*, 113, 1857-1870) and Evin and Weidemann (2002; *Peptides,* 23, 1285-1297). The most common isoforms of Aβ are Aβ40 and Aβ42, 40 and 42 amino acids, respectively. Aβ42 is less common, but is thought to be more fibrillogenic than Aβ40. Effective antibodies may bind both Aβ40 and Aβ42, selectively bind Aβ42, bind all or some isoforms of Aβ, or the like.

Of course it will be understood that antibodies may be directed towards any region of Aβ or selected regions of amyloid precursor protein. In various embodiments, antibodies are directed to an epitope at the N-terminal region of Aβ, e.g., the epitope contains amino acids within 5 amino acids of the N-terminal amino acid. In some embodiments, the epitope lies within amino acids 3-8 of an Aβ peptide and the antibody targets corresponds to amino acids 1-17. In some embodiments, antibodies are directed at the mid-terminal region of Aβ, e.g., the epitope corresponds to amino acids 17-24 of human Aβ. In various embodiments, antibodies are directed to an epitope at the C-terminal region of Aβ, e.g., the epitope corresponds to amino acids 24-40/42/43 of human Aβ or contains amino acids within 5 amino acids of the C-terminal amino acid. In some embodiments, antibodies are directed to intracellular contained Aβ. In numerous embodiments, antibodies are directed towards the extraceullar fraction of Aβ.

The antibodies may be (i) anti-ADDL (Amyloid-beta derived diffusible ligands) antibodies as described in WO/2006/055178, (ii) bapineuzumab n-terminal (Elan &Wyeth), (iii) humanized m266 (LY2062430; Eli Lilly; e.g. as disclosed in U.S. Pat. No. 7,195,761) which binds epitopes 16-24 in the mid section of Aβ, (iv) RN-1219 (PF04360365; Pfizer Rinat) which binds c-terminal epitope of Aβ, (v) fully humanized antibody R-1450 (Knappik et al., 2000; Hoffman-LaRoche/Morphosys), or (vi) the like. The antibodies used in accordance with the teachings provided herein may include non-specific antibodies such as IVIg Gammaguard (Baxter), F(ab')2 fragments (Wilcock et al., 2003), non-antibody Aβ42 binding compounds (Matsuoka et al., 2005), or the like.

Aβ is the main constituent of amyloid plaques in brains of Alzheimer's disease patients. Similar plaques can also be found in some Lewy body dementia patients and Down's Syndrome patients. Similar plaques or Aβ aggregates are found in the cerebral vasculature of cerebral amyloid angiopathy patients. More recent reports describe the accumulation of both soluble and intracellular Aβ ahead of the extracellular amyloid plaques forming (in all of the conditions above) in earlier disease states. In various embodiments, the compositions or methods described herein may be employed to treat or study such diseases.

It will be understood that clearance of soluble forms of Aβ or fibrils or plaques containing Aβ are contemplated. Current models of the physical state of Aβ are evolving. Over about the last 20 years, researchers have defined the soluble toxic species of Aβ according to multiple synonyms. The antibodies described herein may target any of the species defined in Masters and Beyreuther's review (2006), Brain, November; 129(Pt 11):2823-39. Targets include soluble dimmers, tetramers, dodecomers that may ultimately form oligomers, oligomers, amorphous aggregates, Abeta derived diffusible ligands (ADDLS), β-balls, β-Amy balls, globular Aβ oligomer, paranuclei, preamyloid, protofibril, shperocylindrical miscelles, spherical particles, spherical prefibrillar aggregates, and toxic Aβ soluble species.

Antibodies

Any anti-Aβ antibody may be employed in accordance with the teachings presented herein. Representative antibodies include polyclonal, monoclonal, and humanized antibodies.

The term "antibody" is used in the broadest sense and specifically includes, for example, single anti-Aβ monoclonal antibodies (including agonist, antagonist, and neutralizing antibodies), anti-Aβ antibody compositions with poly-epitopic specificity, single chain anti-anti-Aβ antibodies, and fragments of anti-Aβ antibodies (see below). The term "monoclonal antibody" as used herein refers to an antibody obtained from a population of substantially homogeneous antibodies, i.e., the individual antibodies forming the population are identical except for possible naturally-occurring mutations that may be present in minor amounts. An antibody may include an immunoglobulin constant domain from any immunoglobulin, such as IgG-1, IgG-2, IgG-3, or IgG-4 subtypes, IgA (including IgA-1 and IgA-2), IgE, IgD or IgM.

In various embodiments, an antibody includes an IgG-1 immunoglobulin. In many embodiments, an antibody includes an IgG-2 immunoglobulin. In some embodiments, an antibody includes an IgG-4. In numerous embodiments, an antibody includes a combination of various immunoglobulin isotypes, either to a specific epitope of anti-amyloid or broader spectrum IgGs. The structural and functional characteristics that distinguish the IgG subclasses affect the biologic activity of the antibody. For example, several of the IgG subclasses are activators of the classical complement system, although their effectiveness varies. Other distinguishing subclass factors reside in the antibodies ability to bind Fc receptors on phagocytic cells. Further distinctions between immunoglobulin subclasses are demonstrated by their differences in serum half life and pharmacokinetic profile. Tuning the biologic response and efficacy of the antibody to achieve efficacious neutralization or clearance of Aβ can be achieved via selection of the appropriate antibody subclass. For example, an IgG3 tends to be a more effective complement activator yet the function is not required, in and off itself, for efficacy of an anti-Aβ antibody. An IgG4 typically does not activate the classical complement system and, as such, is believed to have an advantage over an IgG3 anti-Aβ antibody in some situations. The IgG1 and IgG4 immunoglobulin represent balance in structural and functional characteristics important for a safe and efficacious passive immunotherapy. Depending on the phase of the patient, either IgG1 or IgG4 anti-Aβ antibodies may be more efficacious. For example, neutralization without complement activation or phagocytosis may be more efficacious in the early phase of therapy where later phases may rely more on phagocytosis of the antigen/antibody complex. Furthermore, complement mediated phagocytosis may be desired when there is an excessive of antibody (Azeredo da Silveira et al., 2002). At higher doses of antibody there may be an increased density of antibody bound to plaques.

In some embodiments, an antibody includes an IgM immunoglobulin. Antibodies having an IgM immunoglobulins may be better able to diffuse into tissue than similar antibodies having an IgG immunoglobulin.

As used herein, an "antibody fragment" means a portion of an intact antibody, most typically the antigen binding or variable region of the intact antibody. Examples of antibody fragments include Fab, Fab', F(ab')$_2$, and Fv fragments; diaries; linear antibodies (Zapata et al., Protein Eng. 8 (10): 1057-1062 [1995]); and single-chain antibody molecules.

Fv" is the minimum antibody fragment which contains a complete antigen-recognition and—binding site. This region consists of a dimer of one heavy- and one light-chain variable domain in tight, non-covalent association. It is in this configuration that the three complementary determining regions (CDRs) of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments include the $V_H$ and $V_L$ domains of antibody, wherein these domains are present in a single polypeptide chain. Preferably, the Fv polypeptide further comprises a polypeptide linker between the $V_H$ and $V_L$ domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically or produced by recombinant DNA technology. See, e.g., Marasco et al., Proc. Natl. Acad. Sci. USA, 90: 7889-7893 (1993).

Any known or developed method for preparing antibodies may be used.

A. Polyclonal Antibodies

Polyclonal antibodies can be raised in a mammal, for example, by one or more injections of an immunizing agent and, if desired, an adjuvant. Typically, the immunizing agent or adjuvant will be injected in the mammal by multiple subcutaneous or intraperitoneal injections. The immunizing agent may include Aβ or fragment or fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

B. Monoclonal Antibodies

Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include Aβ or fragment or fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell, e.g. as described in Goding, Monoclonal Antibodies: Principles and Practice, Academic Press, (1986) pp. 59-103. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Immortalized cell murine myeloma lines can be obtained, for example, from the Salk Institute Cell Distribution Center, San Diego, Calif. and the American Type Culture Collection, Manassas, Va. Human myeloma and mouse-human heteromyeloma cell lines also have been described for the production of human monoclonal antibodies See, e.g., Kozbor, J. Immunol., 133:3001 (1984); and Brodeur et al., Monoclonal Antibody Production Techniques and Applications, Marcel Dekker, Inc., New York, (1987) pp. 51-63.

The culture medium in which the hybridoma cells are cultured can then be assayed for the presence of monoclonal antibodies directed against Aβ. For example, the binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980).

After the desired hybridoma cells are identified, the clones may be subcloned by limiting dilution procedures and grown by standard methods; e.g., as described in Goding, Monoclonal Antibodies: Principles and Practice, Academic Press, (1986) pp. 59-103. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (see, e.g., U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody, or can be substituted for the variable domains of one antigen-combining site of an antibody to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. For example, antibodies may be digested with papain digestion to form F(ab)'$_2$ fragments.

C. Human and Humanized Antibodies

A non-human antibody, such as a mouse antibody, may be recognized by a human patient's immune system as 'foreign' and will therefore be destroyed and will elicit an undersirable immune response. For this reason, the part of the son-human antibody gene responsible for recognizing a specific antigen may be combined with other parts from a human antibody gene. The product of this mouse-human antibody gene, called a "humanized" antibody. This product looks enough like a normal human antibody to avoid being destroyed by the patient's own immune system. This helps the antibody to be effective for longer periods and avoids eliciting a potentially harmful immune response.

Humanized forms of non-human (e.g., murine) antibodies may be chimeric immunoglobulins, immunoglobulin chains or fragments thereof (such as Fv, Fab, Fab', F(ab')$_2$ or other antigen-binding subsequences of antibodies) that contain minimal sequence derived from non-human immunoglobulin or that eliminate or reduce T-cell epitopes from the non-human antibodies. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also include residues which are found neither in the recipient antibody nor in the imported CDR or framework sequences. In general, the humanized antibody will include substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody may also include at least a portion of an immunoglobulin constant region (Fc), typically that of a human immunoglobulin. See, e.g., Jones et al., Nature, 321:522-525 (1986); Riechmann et al., Nature, 332:323-329 (1988); and Presta, Curr. Op. Struct. Biol., 2:593-596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (see, e.g., Jones et al., Nature, 321:522-525 (1986); Riechmann et al., Nature, 332:323-327 (1988); and Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries. See, e.g., Hoogenboom and Winter, J. Mol. Biol., 227:381 (1991); and Marks et al., J. Mol. Biol., 222:581 (1991). Of course other techniques, such as those described by Cole et al. and Boerner et al., are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

The antibodies may also be affinity matured using known selection or mutagenesis methods. Affinity matured antibodies may have an affinity that is five time or more than the starting antibody (generally murine, humanized or human) from which the matured antibody is prepared.

Other methods for humanizing antibodies that may be employed include those described in, e.g., EO0629240, EP0983303, and WO2006/082406 (PCT/GB06/000355), where methods for germ-line humanization and reducing or eliminating T cell epitopes are discussed. One example of humanization of an Aβ antibody using such techniques is presented in U.S. Provisional Patent Application Ser. No. 60/990,401, entitled "HUMANIZED ANTI-AMYLOID BETA ANTIBODIES", filed Nov. 27, 2007, which application is hereby incorporated herein by reference to the extent that it does not conflict with the disclosure provided herein.

Antibody Compositions

Antibodies that specifically bind Aβ can be administered for the treatment of various disorders in the form of pharmaceutical compositions. Such pharmaceutical compositions may also be used for the purposes of investigation, e.g. in vitro or in vivo pre-clinical studies.

Antibodies as described herein can be administered as pharmaceutical compositions that include the antibody and a variety of other pharmaceutically acceptable components. See Remington's Pharmaceutical Science (15th ed., Mack Publishing Company, Easton, Pa. (1980)). The preferred form depends on the intended mode of administration and therapeutic application. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to adversely affect the biological activity of the antibody. Examples of such diluents are distilled water, physiological phosphate-buffered saline, artificial cerebrospinal fluid, citrate buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers or the like.

Pharmaceutical compositions can also include large, slowly metabolized macromolecules such as proteins, polysaccharides such as chitosan, polylactic acids, polyglycolic acids and copolymers (such as latex functionalized sepharose, agarose, cellulose, and the like), polymeric amino acids, amino acid copolymers, and lipid aggregates (such as oil droplets or liposomes). Additionally, these carriers can function as immunostimulating agents (i.e., adjuvants).

For CNS administration, for example intraparenchymal, i.c.v., an intrathecal administration, the compositions are typically formulated as injectable dosages. Injectable compositions include solutions, suspensions, dispersions, or the like. Injectable solutions, suspensions, dispersions, or the like may be formulated according to techniques well-known in the art (see, for example, Remington's Pharmaceutical Sciences, Chapter 43, 14th Ed., Mack Publishing Co., Easton, Pa.), using suitable dispersing or wetting and suspending agents, such as sterile oils, including synthetic mono- or diglycerides, and fatty acids, including oleic acid.

Injectable compositions that include an anti-Aβ antibody may be prepared in water, saline, isotonic saline, phosphate-buffered saline, citrate-buffered saline, or the like and may optionally mixed with a nontoxic surfactant. Dispersions may also be prepared in glycerol, mannitol, liquid polyethylene, glycols, DNA, vegetable oils, triacetin, or the like or mixtures thereof. Under ordinary conditions of storage and use, these preparations may contain a preservative to prevent the growth of microorganisms. Pharmaceutical dosage forms suitable for injection or infusion include sterile, aqueous solutions or dispersions or sterile powders comprising an active ingredient which powders are adapted for the extemporaneous preparation of sterile injectable or infusible solutions or dispersions. Preferably, the ultimate dosage form is a sterile fluid and stable under the conditions of manufacture and storage. A liquid carrier or vehicle of the solution, suspension or dispersion may be a solvent or liquid dispersion medium comprising, for example, water, ethanol, a polyol such as glycerol, propylene glycol, or liquid polyethylene glycols or the like, vegetable oils, nontoxic glyceryl esters, and suitable mixtures thereof. Proper fluidity of solutions, suspensions or dispersions may be maintained, for example, by the formation of liposomes, by the maintenance of the desired particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, or the like. Isotonic agents such as sugars, buffers, or sodium chloride may be included. Prolonged absorption of the injectable compositions can be brought about by the inclusion in the composition of agents delaying absorption; e.g., aluminum monosterate hydrogels or gelatin. Solubility enhancers may be added.

Sterile injectable compositions may be prepared by incorporating an anti-Aβ antibody in the desired amount in the appropriate solvent with various other ingredients, e.g. as enumerated above, and followed by sterilization, as desired, by, for example, filter sterilization. In the case of sterile powders for the preparation of sterile injectable solutions, methods of preparation include vacuum drying and freeze-drying techniques, which yield a powder of the active ingredient plus any additional desired ingredient present in a previously sterile-filtered solution.

In various embodiments, the final solution is adjusted to have a pH between about 4 and about 9, between about 5 and about 7, between about 5.5 and about 6.5, or about 6. The pH of the composition may be adjusted with a pharmacologically acceptable acid, base or buffer. Hydrochloric acid is an example of a suitable acid, and sodium hydroxide is an example of a suitable base. The hydrochloric acid or sodium hydroxide may be in any suitable form, such as a 1N solution A resultant injectable solution preferably contains an amount of one or more anti-Aβ antibodies effective to treat a disease associated with increase or aberrant soluble Aβ or to allow meaningful study of a subject to which the solution is injected. In various embodiments for direct CNS infusion, an anti-Aβ antibody is present in a solution or suspension at a concentration between about 0.001 mg/ml and about 50 mg/ml. In various embodiments, an anti-Aβ antibody is present in a solution or suspension at a concentration between about 0.1 mg/mL and about 10 mg/mL. In various embodiments, an anti-Aβ antibody is present in a solution or suspension at a concentration of about 1 mg/mL.

Of course, anti-Aβ antibodies may be administered to the CNS in the form of a depot injection or implant preparation, which can be formulated in such a manner as to permit a sustained or pulsatile release of the active ingredient.

The formulations discussed above or other formulations containing an anti-Aβ antibody may be administered to a subject via any acceptable route. In various embodiments, a formulation comprising an antibody agent capable of binding Aβ is chronically administered directly to the CNS of a subject. By chronically, it is meant over the course or days, weeks, months, or years. In some circumstances, chronic administration may occur at various times or continuously over the course of administration. In some embodiments, an antibody capable of binding Aβ is chronically administered over the life of the patient after therapy is initiated or until the patient no longer presents symptoms of the treated disease state. As used herein, "direct administration to the CNS", or the like, means delivery of an agent via a delivery region infusion portion of a catheter, where the delivery portion of the catheter is located within the CNS. Example routes of direct CNS administration include intraparenchymal, intrathecal, intracerebroventricular, epidural, or the like. Non-limiting examples of catheters include cannulas, needles, tubes, or the like. A delivery portion of a catheter is typically located at or near a distal end portion of a catheter and may include an opening in fluid communication with a lumen of a catheter.

Delivery Device

In various embodiments, a system including an infusion device is used to deliver a composition containing an anti-Aβ antibody to the CNS of a subject. The system further includes a catheter operably coupled to the infusion device. The infusion device may be a pump device. Non-limiting examples of pump devices include osmotic pumps, fixed-rate pumps, programmable pumps and the like. Each of the aforementioned pump systems conatin a reservoir for housing a fluid composition containing the anti-Aβ antibody. The catheter includes one or more delivery regions, through which the fluid may be delivered to one or more target regions of the subject. The pump device may be implantable or may be placed external to the subject.

An infusion device 30 according to various embodiments is shown in FIG. 1 and includes a reservoir 12 for housing a composition and a pump 40 operably coupled to the reservoir 12. The catheter 38 shown in FIG. 2 has a proximal end 35 coupled to the therapy delivery device 30 and a distal end 39 configured to be implanted in a target location of a subject. Between the proximal end 35 and distal end 39 or at the distal end 39, the catheter 38 has one or more delivery regions (not shown), such as openings, through which the composition may be delivered. The infusion device 30 may have a port 34 into which a hypodermic needle can be inserted to inject a composition into reservoir 12. The infusion device 30 may have a catheter port 37, to which the proximal end 35 of catheter 38 may be coupled. The catheter port 37 may be operably coupled to reservoir 12. A connector 14 may be used to couple the catheter 38 to the catheter port 37 of the infusion device 30. The infusion device 30 may be operated to discharge a predetermined dosage of the pumped fluid into a target region of a subject. The infusion device 30 may contain a microprocessor 42 or similar device that can be programmed to control the amount of fluid delivery. The programming may be accomplished with an external programmer/control unit via telemetry. A controlled amount of fluid may be delivered over a specified time period. With the use of a programmable infusion device 30, dosage regimens may be programmed and tailored for a particular patient. Additionally, different therapeutic dosages can be programmed for different combinations of fluid comprising therapeutics. Those skilled in the art will recognize that a programmable infusion device 30 allows for starting conservatively with lower doses and adjusting to a more aggressive dosing scheme, if warranted, based on safety and efficacy factors. While not shown, device 30 may include a catheter access port to allow for direct delivery of a composition including an anti-Aβ antibody via catheter 38.

Figure 2:
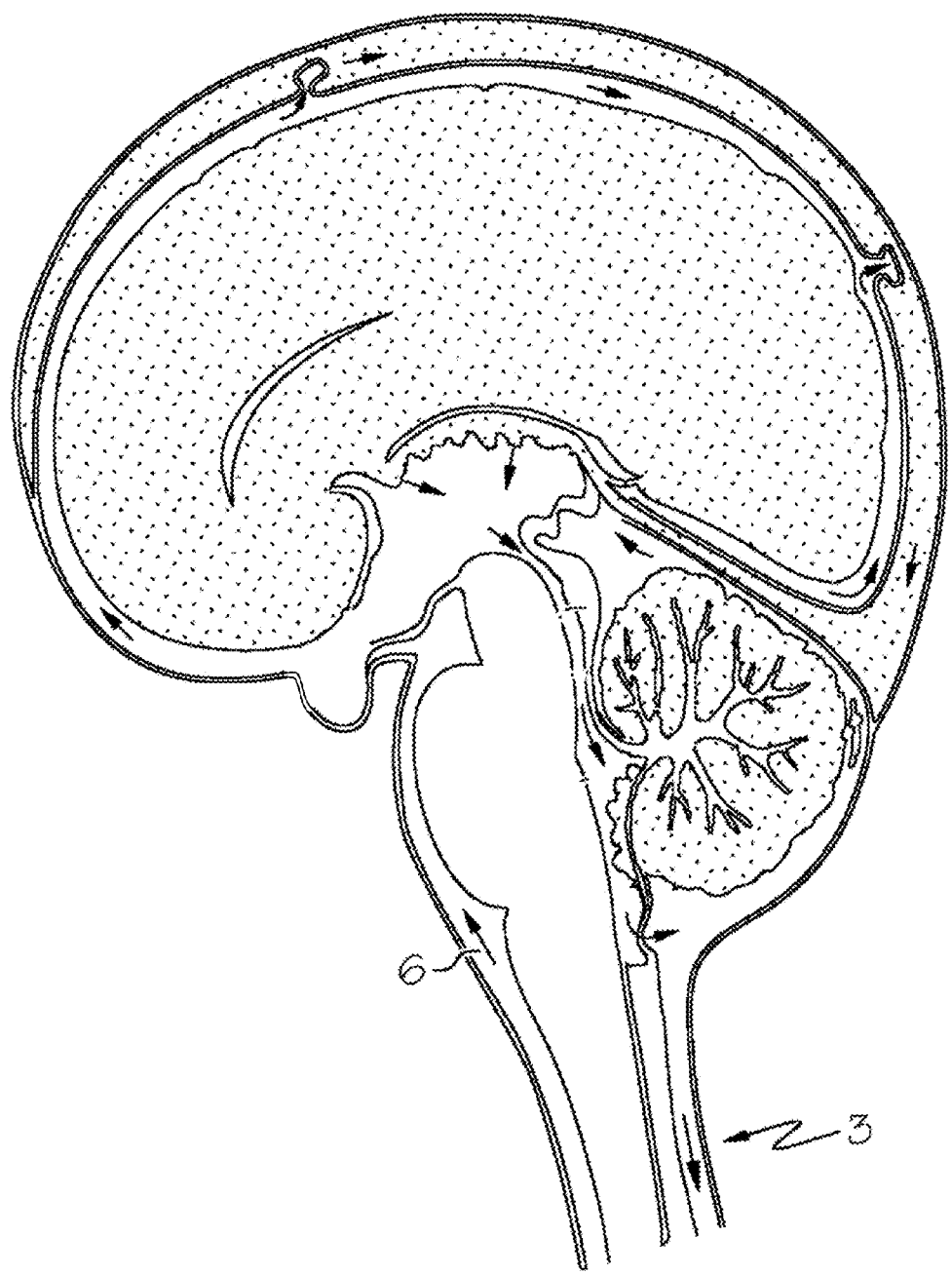
FIG. 2 is a drawing of a schematic section of a brain and portions of a spinal cord showing cerebrospinal fluid flow.

According to various embodiments, a composition comprising an anti-Aβ antibody may be delivered directly to cerebrospinal fluid 6 of a subject. Referring to FIG. 2, cerebrospinal fluid (CSF) 6 exits the foramen of Magendie and Luschka to flow around the brainstem and cerebellum. The arrows within the subarachnoid space 3 in FIG. 2 indicate cerebrospinal fluid 6 flow. The subarachnoid space 3 is a compartment within the central nervous system that contains cerebrospinal fluid 6. The cerebrospinal fluid 6 is produced in the ventricular system of the brain and communicates freely with the subarachnoid space 3 via the foramen of Magendie and Luschka. A composition containing an anti-Aβ antibody may be delivered to cerebrospinal fluid 6 of a subject anywhere that the cerebrospinal fluid 6 is accessible. For example, the composition may be administered intrathecally or intracerebroventricularly.

Figure 3:
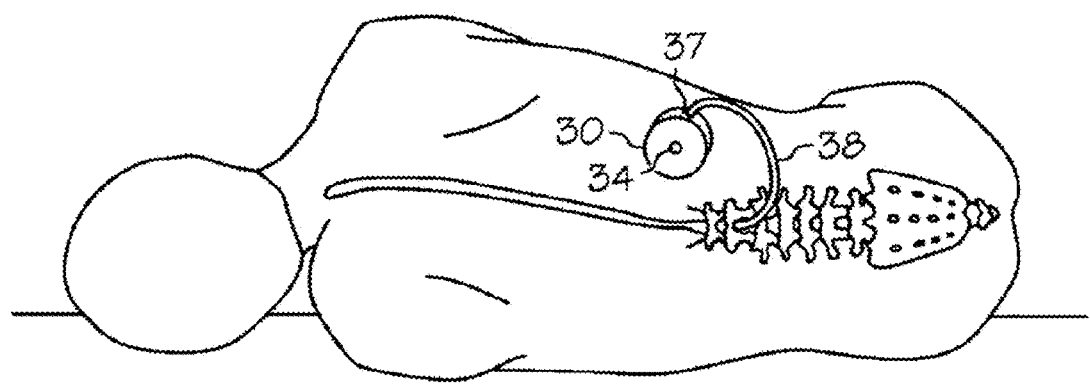
FIG. 3 is a drawing of a schematic view of an infusion device and associated catheter implanted in a patient.

FIG. 3 illustrates a representative system configured for intrathecal delivery of a composition containing an anti-Aβ antibody. As shown in FIG. 3, a system or device 30 may be implanted below the skin of a patient. Preferably the device 30 is implanted in a location where the implantation interferes as little as practicable with activity of the subject in which it is implanted. One suitable location for implanting the device 30 is subcutaneously in the lower abdomen. In various embodiments, catheter 38 is positioned so that the distal end 39 of catheter 38 is located in the subarachnoid space 3 of the spinal cord such that a delivery region (not shown) of catheter is also located within the subarachnoid space 3. It will be understood that the delivery region can be placed in a multitude of locations to direct delivery of an agent to a multitude of locations within the cerebrospinal fluid 6 of the patient. The location of the distal end 39 and delivery region(s) of the catheter 38 may be adjusted to improve therapeutic efficacy.

According to various embodiments, a composition containing an anti-Aβ antibody may be delivered intraparenchymally directly to brain tissue of a subject. An infusion device may be used to deliver the agent to the brain tissue. A catheter may be operably coupled to the infusion device and a delivery region of the catheter may be placed in or near a target region of the brain.

Figure 4:
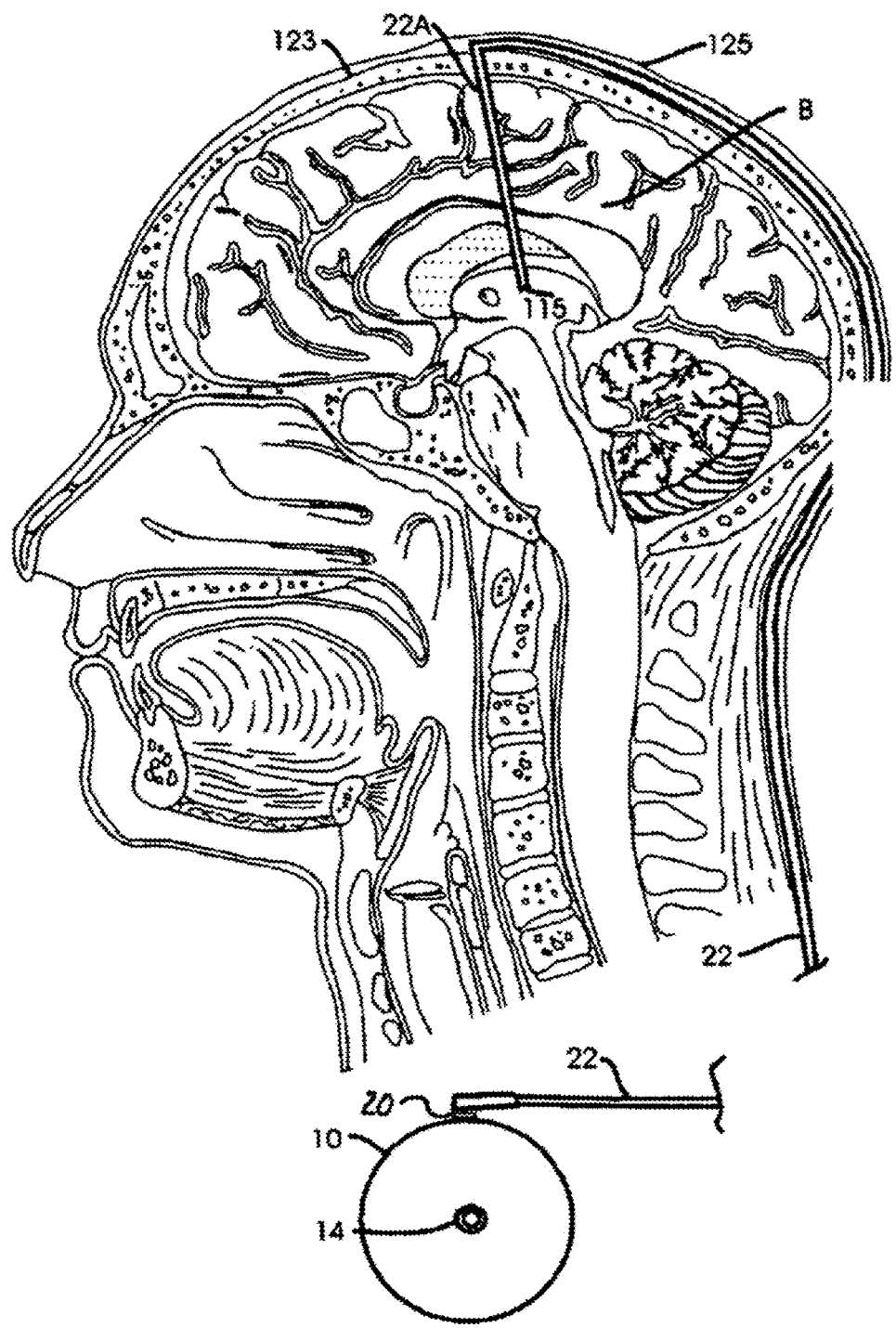
FIG. 4 is a drawing of a schematic view of a section of a patient showing an implanted infusion device and associated catheter implanted.

One suitable system for administering a therapeutic agent to the brain is discussed in U.S. Pat. No. 5,711,316 (Elsberry). Referring to FIG. 4, a system or infusion device 10 may be implanted below the skin of a subject. The device 10 may have a port 14 into which a hypodermic needle can be inserted through the skin to inject a quantity of a composition comprising a therapeutic agent. The composition is delivered from device 10 through a catheter port 20 into a catheter 22. Catheter 22 is positioned to deliver the agent to specific infusion sites in a brain (B). Device 10 may take the form of the like-numbered device shown in U.S. Pat. No. 4,692,147 (Duggan), assigned to Medtronic, Inc., Minneapolis, Minn., or take the form of a SynchroMed II infusion device (Medtronic, Inc.). The distal end of catheter 22 terminates in a cylindrical hollow tube 22A having a distal end 115 implanted into a target portion of the brain by conventional stereotactic surgical techniques. Additional details about end 115, according to various embodiments, may be obtained from U.S. application Ser. No. 08/430,960 entitled "Intraparenchymal Infusion Catheter System," filed Apr. 28, 1995 in the name of Dennis Elsberry et al. and assigned to the same assignee as the present application. Tube 22A is surgically implanted through a hole in the skull 123 and catheter 22 is implanted between the skull and the scalp 125 as shown in FIG. 4. Catheter 22 may be coupled to implanted device 10 in the manner shown or in any other suitable manner.

Figure 5:
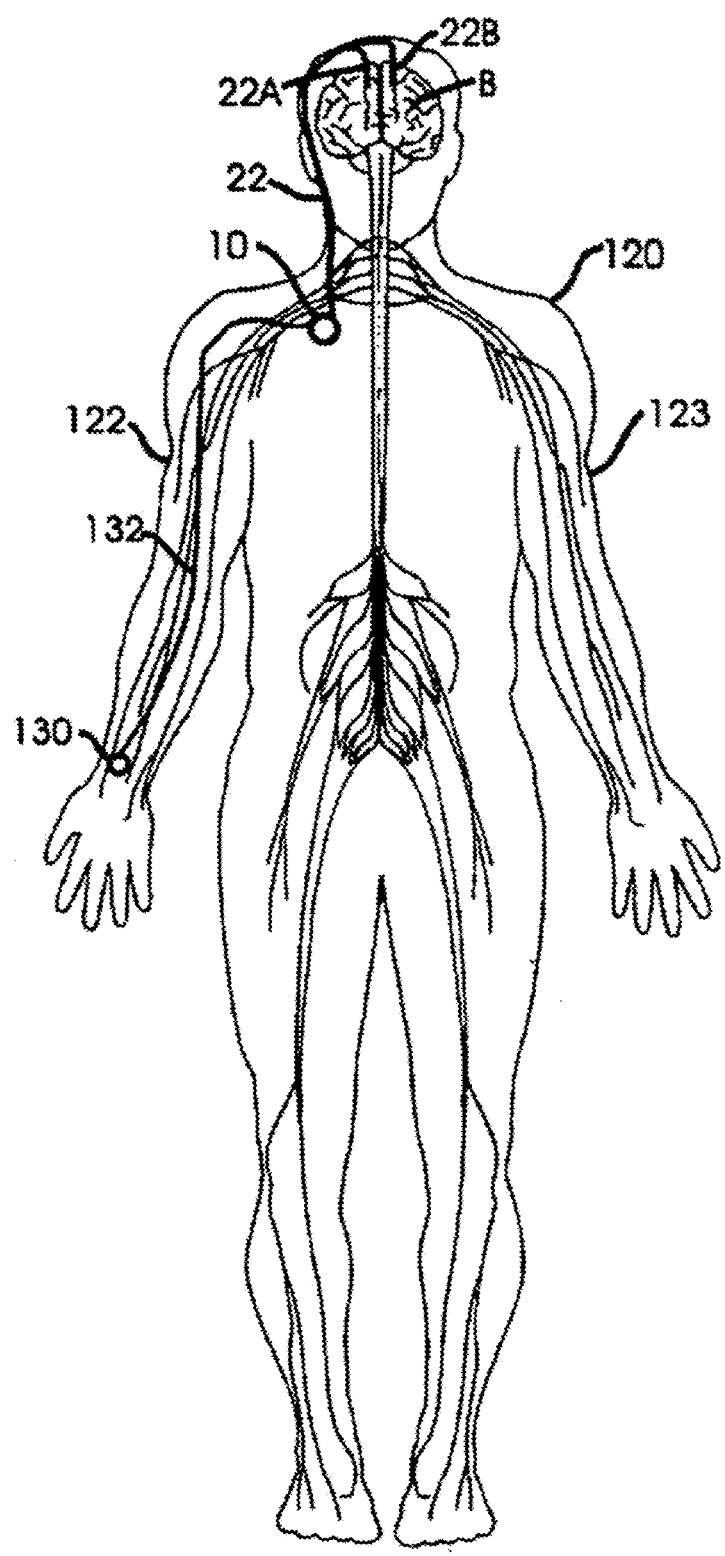
FIG. 5 is a drawing of a schematic view showing an implanted infusion device and associated catheter in the environment of a patient.

Referring to FIG. 5, a therapy delivery device 10 is implanted in a human body 120 in the location shown or may be implanted in any other suitable location. Body 120 includes arms 122 and 123. In various embodiments and as depicted, catheter 22 is divided into twin or similar tubes 22A and 22B that are implanted into the brain bilaterally. In some embodiments, tube 22B is supplied with a composition from a separate catheter and pump. Of course, unilateral delivery may be performed in accordance with the teachings presented herein.

Figure 5A:
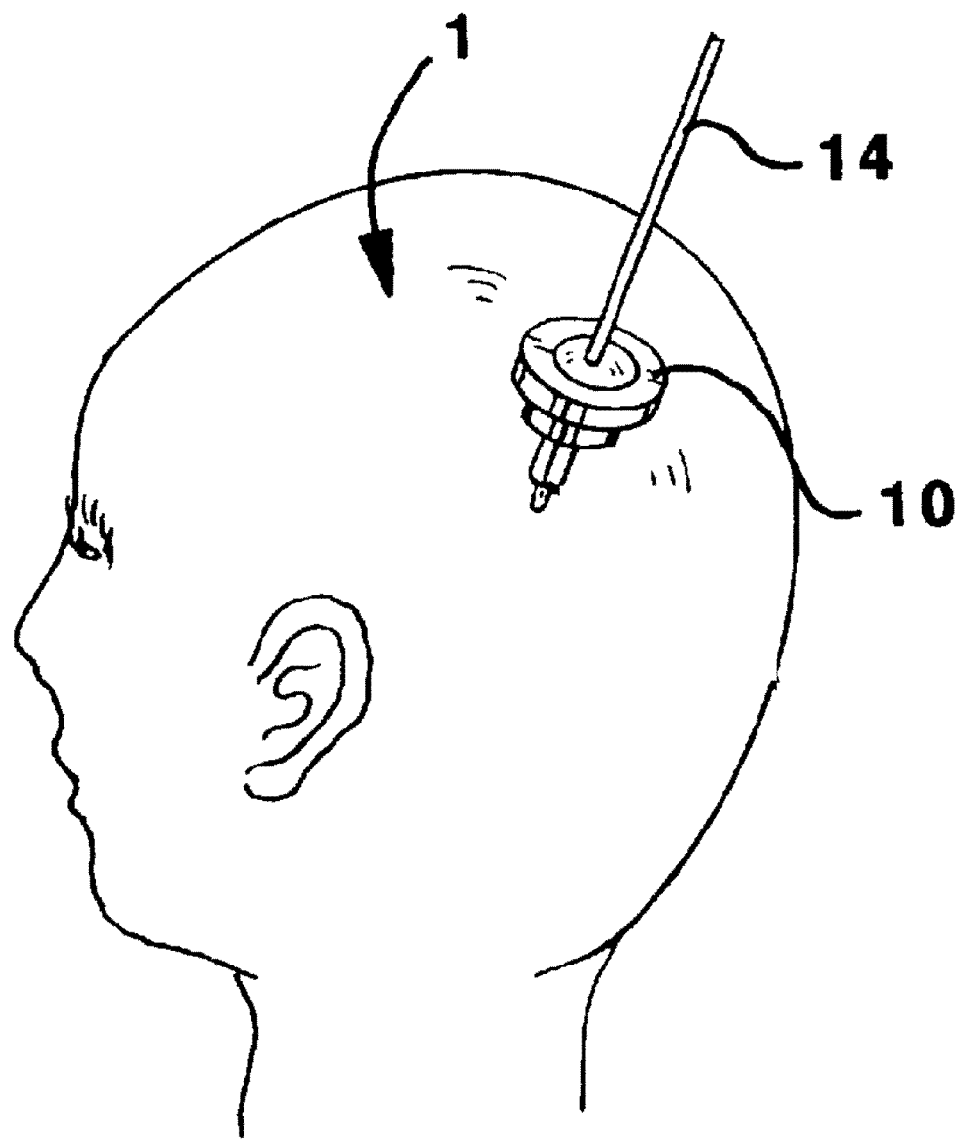
FIG. 5A is a drawing of a schematic view showing an injection port in the environment of a patient.

Referring to FIG. 5A, an anti-Ab antibody may be delivered to a subject's CNS via an injection port 10 implanted subcutaneously in the scalp of a patient 1, e.g. as described in U.S. Pat. No. 5,954,687 or otherwise known in the art. A guide catheter 10 may be used to guide an infusion catheter through port 10 to a target location. Of course, an infusion catheter may be directly be inserted through port 10 to the target location.

Any other known or developed implantable or external infusion device or port may be employed.

Figure 6:
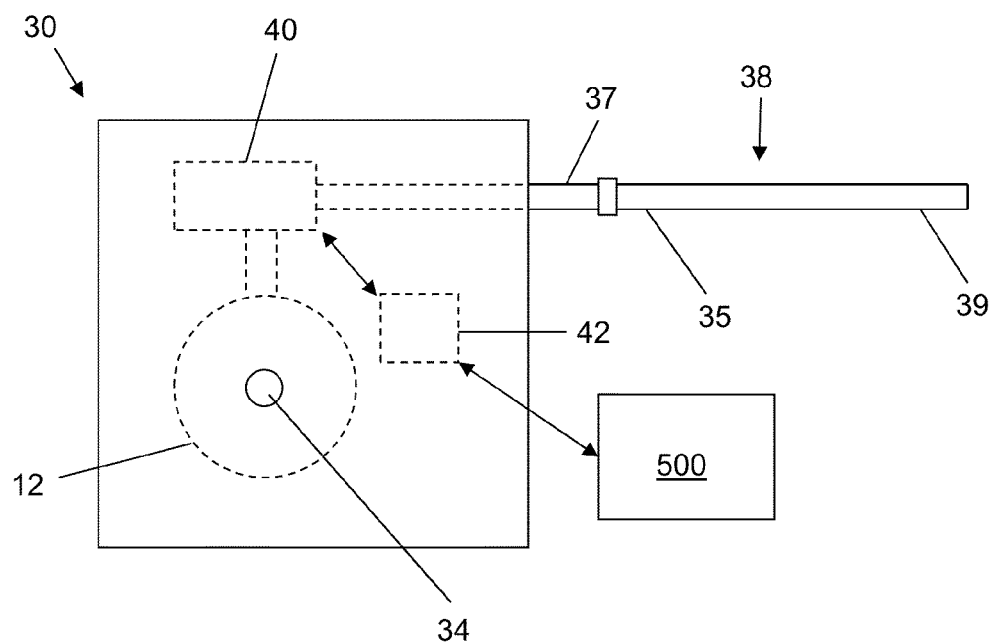
FIG. 6 is a drawing of a schematic side view of a representative system including an infusion device and a sensor.

Referring to FIG. 6, a representative system including an infusion device 30 and a sensor 500 is shown. The sensor 500 may detect an attribute of the nervous system, which attribute may reflect a pathology associated with a disease to be treated or studied or the amount of antibody already in the targeted region. A microprocessor 42 may analyze output from the sensor 50 and regulate the amount of antibody delivered to the brain. Sensor 500 may be operably coupled to processor 42 in any manner. For example, sensor 500 may be connected to processor via a direct electrical connection, such as through a wire or cable, or via wireless communication. Sensed information, whether processed or not, may be recoded by device 30 and stored in memory (not shown). The stored sensed memory may be relayed to an external programmer, where a physician may modify one or more parameter associated with the therapy based on the relayed information. Alternatively, based on the sensed information, processor 42 may adjust one or more parameters associated with therapy delivery. For example, processor 42 may adjust the amount or timing of the infusion of an anti-Aβ antibody. It will be understood that two or more sensors 500 may be employed.

Sensor 500 may detect a polypeptide associated with a CNS disorder to be treated or investigated; a physiological effect, such as a change in membrane potential; a clinical response, such as blood pressure; or the like. In various embodiments, a component of an infused composition, such as the anti-Aβ antibody or other component, which may be added specifically for the purpose of detection by the sensor 500, is detected. Any suitable sensor 500 may be used. A biosensor may be used to detect the presence of a polypeptide or other molecule in a patient. Any known or future developed biosensor may be used. The biosensor may have, e.g., an enzyme, an antibody, a receptor, or the like operably coupled to, e.g., a suitable physical transducer capable of converting the biological signal into an electrical signal. In some situations, receptors or enzymes that reversibly bind the molecule being detected may be preferred. In various embodiments, sensor 500 is a sensor as described in, e.g., U.S. Pat. No. 5,978,702, entitled TECHNIQUES OF TREATING EPILEPSY BY BRAIN STIMULATION AND DRUG INFUSION, or U.S. patent application Ser. No. 10/826,925, entitled COLLECTING SLEEP QUALITY INFORMATION VIA A MEDICAL DEVICE, filed Apr. 15, 2004, or U.S. patent application Ser. No. 10/820,677, entitled DEVICE AND METHOD FOR ATTENUATING AN IMMUNE RESPONSE, filed Apr. 8, 2004.

Examples of sensor technology that may be adapted for use in some embodiments include those disclosed in: (i) U.S. Pat. No. 5,640,764 for "Method of forming a tubular feedthrough hermetic seal for an implantable medical device;" (ii) U.S. Pat. No. 5,660,163 for "Glucose sensor assembly;" (iii) U.S. Pat. No. 5,750,926 for "Hermetically sealed electrical feedthrough for use with implantable electronic devices;" (iv) U.S. Pat. No. 5,791,344 for "Patient monitoring system;" (v) U.S. Pat. No. 5,917,346 for "Low power current to frequency converter circuit for use in implantable sensors;" (vi) U.S. Pat. No. 5,957,958 for "Implantable electrode arrays;" (vii) U.S. Pat. No. 5,999,848 for "Daisy chainable sensors and stimulators for implantation in living tissue;" (viii) U.S. Pat. No. 6,043,437 for "Alumina insulation for coating implantable components and other microminiature devices;" (ix) U.S. Pat. No. 6,088,608 for "Electrochemical sensor and integrity tests therefor;" or (x) U.S. Pat. No. 6,259,937 for "Implantable substrate sensor."

Methods

Chronically administering an antibody capable of binding Aβ in the CNS of a subject as described herein or according to any other known or developed technique may be used to treat or study a disease associated with increased or aberrant soluble Aβ, amyloid fibrils or amyloid plaques. Examples of disease associated with increased or aberrant soluble Aβ, amyloid fibrils or amyloid plaques include Alzheimer's disease (AD), cerebral amyloid angiopathy (CAA), Lewy body dementia, and Down's Syndrome (DS).

Any amount of antibody effective to bind Aβ, whether soluble, in fibrils, plaques, or the like may be employed. In general, a daily dose of between about 0.0001 and about 1 mg of the antibody per kg of the subject's body weight will be effective. In various embodiments, daily doses of between about 0.001 and about 1, between about 0.01 and 0.1, or between about 0.1 and about 1 mg of the antibody per kg of the subject's body weight are administered to the subject's CNS. The above daily doses should be generally effective for intracerebroventricular (i.c.v.) delivery to a lateral ventrical of the subject. For intrathecal delivery, increased dosages may be warranted. For example, daily dosages may be increased by about 20% relative to i.c.v. Any other suitable modification in dosing based on route of administration, such as intraparenchymal, in comparison to i.c.v. may be employed.

An injectable composition including an anti-Aβ antibody may be delivered at any suitable rate. For chronic delivery to the CNS, the composition is typically delivered at a rate of 0.01-15 ml/day, 0.01-5 ml/day, or 0.01-1 ml/day. It will be understood that the concentration of the anti-Aβ antibody in the composition may be adjusted, based on the delivery rate, to achieve a desired daily dose. The rate of delivery may be constant or may be variable. In various embodiments, delivery includes periods of increased delivery rate (e.g., pulsed boluses) on top of a constant lower rate. Such pulsed boluses may readily be achieved with a programmable infusion device such as the SynchroMed II infusion device (Medtronic, Inc.). Such pulsed bolus administration may result in improved distribution of the delivered antibody relative to constant rate delivery due to increased convection. In some embodiments, the antibody may be delivered for a period of time, the delivery may then be halted, and then resumed. For example, the antibody may be delivered for one hour to one week, delivery may then be halted for one hour to one week, and so on. Such a dosing scheme may serve to prolong the delivery life of the antibody, as the half life of the delivered antibody may be considerably shorter than the half life of an antibody housed in a reservoir of an infusion device.

In some embodiments, the mode of delivery may be altered during the course of treatment. For example, the antibody may be delivered i.c.v. at one stage of treatment and delivered intraparenchymally (i.p.a) at another stage of treatment, as conditions warrant. For example if it is desired to obtain microglial activation to clear of Aβ, i.p.a. administration may be desired. If clearance via a CSF sink is desired, i.c.v. administration may be desired. Alternatively, or in addition, an antibody may be delivered i.c.v. and i.p.a at the same time. Regardless of whether the route of administration is altered or if delivery is accomplished simultaneously via two routes, it may be desirable to implant a delivery region of a catheter intraparenchymally and implant a delivery region of the same (e.g., split catheter) or different catheter in the CSF at the time of initial implant.

In various embodiments a method includes identifying a subject suffering from or at risk of AD and chronically delivering to the CNS of the subject an antibody directed to Aβ. Those at risk of AD include those of advancing age, family history of the disease, mutations in APP or related genes, having heart disease risk factors, having stress or high levels of anxiety. Identification of those suffering from or at risk of AD can be readily accomplished by a physician. Diagnosis may be based on mental, psychiatric and neuropyschological assessments, blood tests, brain imaging (PET, MRI, CT scan), urine tests, tests on the cerebrospinal fluid obtained through lumbar puncture, or the like.

In various embodiments a method includes identifying a subject suffering from or at risk of CAA and chronically delivering to the CNS of the subject an antibody directed to Aβ Symptoms of CAA include weakness or paralysis of the limbs, difficulty speaking, loss of sensation or balance, or even coma. If blood leaks out to the sensitive tissue around the brain, it can cause a sudden and severe headache. Other symptoms sometimes caused by irritation of the surrounding brain are seizures (convulsions) or short spells of temporary neurologic symptoms such as tingling or weakness in the limbs or face. CAA patients can be identified by, e.g., examination of an evacuated hematoma or brain biopsy specimen, the frequency of APOE ε2 or ε4 alleles, with clinical or radiographic (MRI and CT scans) grounds according the Boston Criteria (Knudsen et al., 2001, Neurology; 56:537-539), or the like. Those at risk of CAA include those of advancing age, those having the APOE genotype, and those having other risk factors associated with AD.

In various embodiments a method includes identifying a subject suffering from or at risk of Down Syndrome and chronically delivering to the CNS of the subject an antibody directed to Aβ. A newborn with Down Syndrome can be identified at birth by a physician's physical exam. The diagnosis may be confirmed through kariotyping. Multiple screening tests may be used to test or diagnosis a patient prior to birth (biomarkers, nuchal translucency, amniocentesis, etc.). A Down's Syndrome patient may be diagnosis with AD using diagnostic criteria relevant for AD.

In various embodiments a method includes identifying a subject suffering from or at risk of Lewy body dementia and chronically delivering to the CNS of the subject an antibody directed to Aβ. Those suffering from or at risk of Lewy body dementia can be identified by mental, psychiatric or neuro-pyschological assessments, blood tests, brain imaging (PET, MRI, CT scan), urine tests, tests on the cerebrospinal fluid obtained through lumbar puncture, or the like. Those at risk of Lewy body dementia include those of advancing age.

In various embodiments, cerebral plaques may be cleared or prevented from forming by administering anti-Aβ antibodies to a subject's CNS. It will be understood that achieving any level of clearing of a plaque or plaques will constitute clearing of the plaque or plaques. It will be further understood that achieving any level of prevention of formation of a plaque or plaques will constitute preventing formation of the plaque or plaques. Accordingly, in various embodiments, methods for clearing plaques include delivering, to a subject in need thereof, an amount of an anti-Aβ antibody effective in clearing the plaques. In various embodiments, methods for preventing the formation of plaques include delivering, to a subject in need thereof, an amount of an anti-Aβ antibody effective in preventing the formation the plaques. The methods may further include clearing or preventing parenchymal amyloid plaques or soluble forms of Aβ. The methods may further include improving cognitive aspects of the subject.

In various embodiments, cognitive abilities of a subject are improved by administering anti-Aβ antibodies to a subject's CNS.

In various embodiments, parenchymal amyloid plaques or soluble forms of Aβ are cleared in a subject by administering anti-Aβ antibodies to a subject's CNS.

The ability of a therapy described herein to treat a disease may be evaluated through medical examination, e.g. as discussed above, or by diagnostic or other tests. In various embodiments, a method as described in WO 2006/107814 (Bateman et al.) is performed. For example, a subject may be administered radiolabeled leucine. Samples, such as plasma or CSF, may then be obtained to quantify the labeled-to-unlabeled leucine in, for example, amyloid beta or other key disease related biomarkers, to determine the production and clearance rate of such proteins or polypeptides.

Clearing of, or formation of, amyloid beta can be evaluated in vivo by structural or functional neuro-imaging techniques. For example, diffusion tensor MRI (reviewed in Parente et al., 2008; Chua et al., 2008), PET imaging with the Aβ binding compound, Pittsburgh Compound B (PiB, Klunk et al., 2004; Fagan et al., 2006; Fagan et al 2007) or other SPECT based imaging of fibrillar Aβ structures and measurement of CSF levels of Aβ42 or tau may be employed. Distribution of vascular Aβ may be evaluated using differential interpretation of PET imaging of PiB (Johnson et al., 2007). Additionally, a cerebral microhemorrahage may be recognized by on gradient-echo or T-2 weighted MRI sequences (Viswanathan and Chabriat, 2006).

Similarly, detection of hemorrhages of the cerebral vasculature can be evaluated by imaging techniques, clinical evaluation, or the like. Spontaneous intracerebral hemorrhage (ICH) usually results in a focal neurologic deficit and is easily diagnosed on clinical and radiographic grounds (computed tomography (CT) scan, T-2 weighted MRI). Cerebral microhemorrhage results from underlying small vessel pathologies such as hypertensive vasculpathy or CAA. Cerebral microhemorrhages, best visualized by MRI, result from rupture of small blood vessels. The MRI diagnosis can be variable as described by Orgagozo et al., 2003 (Subacute meningoencephalitis in a subset of patients with AD after Aβ42 immunization-Elan Trial). For instance, patients showing signs and symptoms of aseptic meningoencephalitis MRIs showed only meningeal enhancement, whereas others had meningeal thickening, white matter lesions, with or without enhancing or edema, and a majority had posterior cerebral cortical or cerebellar lesions. Other potential diagnostics include changes in intracranial pressure, which may be detected by specific MRI techniques (Glick, et al., 2006, Alperin) or other standard techniques as described in Method of detecting brain microhemmorhage (U.S. Pat. No. 5,951,476).

EXAMPLES

Example 1

Pilot Study for Evaluating Dose and Time Effects of Aβ Antibodies Acutely Infused into the Lateral Ventricle of a Transgenic Model of Alzheimer's Disease Behavioral and pathological changes in Tg2576 mice following infusion of increasing doses of anti-Aβ $IgG_1$ or its $F(ab)'_2$ fragments into the lateral ventricle were determined at various time points. Anti-Aβ $IgG_1$ produced a bilateral, dose- and time-dependent reduction of the cerebral Aβ plaque load, with an effect lasting up to 8 weeks post-injection of the highest dose (12 μg). An increase in the vascular Aβ load and incidence of microhemorrhage were noted with the high dose of anti-Aβ $IgG_1$. Infusions of equimolar anti-Aβ $IgG_1$-$F(ab')_2$ produced a short-lasting (up to 1 week), yet similar decrease in the cerebral Aβ levels, but was devoid of any deleterious effects related to the cerebral vasculature. In addition, elevated plasma Aβ levels were observed at 8 weeks post-injection, along with a behavioral improvement in the Y maze alternation task. Treatment-induced changes in other pathological indices (e.g. astrogliosis) correlated with the changes in cerebral Aβ accumulation.

1. Experimental Design

A. Experimental Groups

Animals were split into four groups according to antibody and dose administered as follows: (1) Anti-Aβ $IgG_1$ (6 μg); (2) Anti-Aβ $IgG_1$ (12 μg); (3) Anti-Aβ $IgG_1$ $F(ab)'_2$ (8 μg), which represented an equivalent molar amount to the group receiving 12 μg Anti-Aβ $IgG_1$; and (4) control $IgG_1$ (12 μg). The in-life period for each experimental group was 1, 4, and 8 weeks post-infusion. The anti-Aβ antibodies were directed to the N-terminus and bind an epitope within the first 16 amino acids of Aβ.

48 Tg2576 mice (Taconic, Hudson, N.Y.) were split equally into the above experimental groups. Four mice within each group were assigned to each of the three time points (4 experimental groups×3 time-points post-infusion×4 mice per group=48 mice).

Tg2576 mice encode a human β-amyloid precursor protein (βAPP)-695 isoform with a K670N/M671L mutation and mimic several behavioral as well as biochemical characteristics of AD. The age of onset and development of complete pathology is typically between about 10-13 months or more.

Male Tg2576 mice, aged 12-14 months were used for stereotaxic infusion of test article into the lateral ventricle. All mice were subcutaneously implanted with AVID identification microchips. Each mouse was also ear-punched for confirmation of the transgenic genotype. Surgical infusions were performed over a period of 6 days with a thorough randomization of experimental groups among mice with different dates of birth and also among the number of surgeries per day. Mice were tail-marked, using a permanent marker, for identifying them with a number assigned during the study. However, the AVID microchips remained the primary source of mouse identification.

B. Administration of Test Article

On each surgery day, mice were administered with an analgesic dose of buprenorphine (0.05 mg/kg, i.p.) at least 30 min prior to administering the anesthetic (a mixture of ketamine, 100 mg/kg, and xylazine, 10 mg/kg, i.p.). The mouse was prepared for surgical administration of the test article within 5 min of injecting the anesthetic. Briefly, the head of the mouse was shaved and disinfected with a topical antiseptic, Xenodine (Veterinary Products Laboratories), and the mouse mounted on a stereotaxic frame. A skin incision was made on the head, and the underlying tissue cleared to expose the Bregma and Lambda. A burr hole was drilled on the skull for injection into the coordinates; AP: −0.4 mm, ML: +1.0 mm, and DV: −2.3 mm, relative to Bregma. The test article was administered using a pre-filled, pump-regulated Hamilton micro-syringe (7654-01) connected to a 33 gauge needle.

Parameters for administering the experimental article were as follows. Briefly, a needle was manually inserted at the rate of ~0.01 mm/sec (possible upon using a digital stereotaxic coordinate recorder). Once the distal end of the needle reached the target location, 16 μl of the test article was infused. For Group 1, 6 μl (1 μg/μl) of Anti-Aβ $IgG_1$ was diluted in 10 μl of sterile PBS. For Group 2, 12 μl (1 μg/μl) of Anti-Aβ $IgG_1$ was diluted in 10 μl of sterile PBS. For Group 3, 16 μl (0.5 μg/μl) of Anti-Aβ $IgG_1$ $F(ab')_2$ was infused. For Group 4, 12 μl (1 μg/μl) of Control $IgG_1$ was diluted in 4 μl of sterile PBS. For all groups, the test article was infused at a rate of 0.5 μl/min over 32 min. Five minutes following infusion, the needle was withdrawn at a rate of approximately 0.01 mm/sec.

The burr hole was sealed using dental cement, and the skin on top was sutured. After administering sterile 5% dextrose in saline (1 ml, i.p.), the mouse was placed in a cage, with its floor maintained at 37° C., for recovery from anesthetic (1-2 h). Thereafter, each mouse was singly housed with a food pellet and an aluminum dish, filled with water, placed inside the cage.

C. Behavioral Analyses

Assigning the day of termination as day 0, behavioral analyses of mice were performed starting day −2 as follows:

i. Y-Maze Alternation Tests

Y-maze alternation tests for up to 10 min. were performed on day −2 as described in Ognibene et al. (2005), *Behav. Brain Res.* 156, 225-232. The Y-maze alternation test may be used to detect a hippocampus-dependent tendency of rodents to explore the 3 different arms of a Y-shaped maze in each set of alternation. Tg2576 mice have been demonstrated to exhibit a deficit in this alternation task (Ognibene et al. (2005)).

ii. Spatial Object Location Memory Test

Spatial object location memory tests present a cognitive challenge of exploring objects that are familiar (previously exposed to the object) but arranged in a different spatial context. This paradigm evaluates memory and cognitive functions dependent on the hippocampus as well as cortex, and has revealed a deficit in the Tg2576 mice (e.g. Hale and Good (2005), *Behav. Neurosci.* 119, 884-891; Ognibene et al., (2005)). The spatial object location memory test was performed as described (Hale and Good, 2005) on day −1 just 3 min after testing the locomotor activity of mice (see below) in an arena 40 cm long, 40 cm wide, and 40 cm high (Coulbourn Instruments, Allentown, Pa.). In brief, mice were allowed to explore 4 different objects placed at 4 corners of a hypothetical square with sides that were at least 10 cm distant from the walls of the arena. After 10 min of initial exploration, mice were placed back into their home cages for 3 min, during which, the positions of any 2 diagonally opposite objects were switched. Mice were then assessed for an additional 10 min for exploring the differentially placed objects in the arena.

ii. Locomotor Activity Test

Locomotor activity was evaluated in terms of horizontal distance traveled for up to 1 hr upon placement of the subject mouse in a novel environment (arena discussed above) using the Limelight system (Coulbourn Instruments, Allentown, Pa.). Potential adverse effects of the treatment on the animal's gross physiological or psychiatric attributes can be detected with this behavior. Changes in locomotor activity resulting from administration of the test article may confound the outcomes of all the above-mentioned behavioral tests.

D. Termination Procedure for Tissue Collection and Processing

Mice were anesthetized using ketamine/xylazine, as described earlier, at the desired time point following acute infusion of the test article. Trans-cardial perfusions were performed in mice with PBS, wherein the first 20 ml of PBS-diluted blood from the animal was collected, followed by infusion with paraformaldehyde (4% in PBS). Thereafter, the brains were removed on a dish maintained at 4° C.

The PBS-diluted blood samples were centrifuged and serum was frozen at −80° C., under dry ice, until testing by ELISAs to detect levels of $A\beta_{1-40}$, $A\beta_{1-42}$, as well as presence of the infused test article.

The brains were individually incubated in paraformaldehyde (4% in PBS) overnight at 4° C. Thereafter, paraformaldehyde was replaced with PBS containing sodium azide (0.01%), and the brains stored at 4° C. until sectioning and immunohistochemical analyses.

E. Qualitative Analyses:

Brains were coronally sectioned, by NeuroScience Associates (NSA), at 40 μm thickness/section across the entire rostra-caudal axis, and sections at intervals of ~360 μm were stained as follows. Briefly, Campbell Switzer stain was used to label diffuse and dense-core Aβ plaques in brain parenchyma as well as vasculature. Aβ was used to label diffuse and dense-core Aβ plaques in the brain parenchyma. Glial fibrillary acidic protein (GFAP) was used to label astrocytes. CD45 and Iba1 were used to label inflammatory microglial response. Perl's diaminobenzidine (DAB) was used to label hemosiderin-positive cells as a marker for microhemorrhages. All sections spanning the cortical and hippocampal nuclei across the entire rostra-caudal axis of the mouse brain (~7 mm) were analyzed for each stain.

2. Results

One Group 1 mouse, one Group 2 mouse, and one Group 3 mouse died prior to their desired termination period of 4 weeks; at 2, 2.5, and 3.5 weeks post-infusion, respectively. Similarly, one Group 1 mouse died a day earlier than its desired termination at 1 week. The cause of the pre-mature death of these mice remains undetermined, although, with an observation of discolored gastro-intestinal tract or heart during their necropsy. These events are unlikely to occur from the infusion of experimental treatments, as no such deaths were observed in any groups terminated 8 weeks post-infusion. Furthermore, a similar discoloration of organs and even enlargement of spleen or seminal vesicles has been observed for most of the non-experimental transgenic as well as wild-type mice that have died during their normal aging (>12 months) process.

Figure 7:
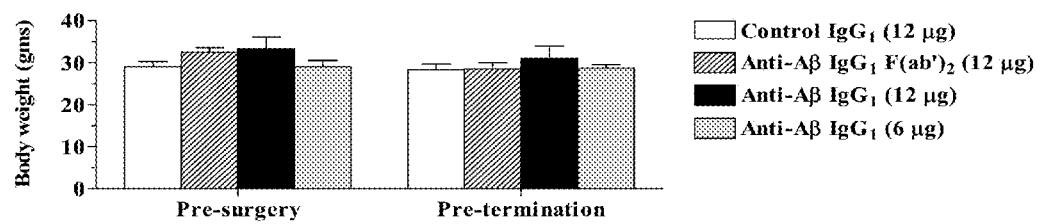
FIG. 7 includes panels A-C of bar graphs showing body weight of mice 1 week (A), 4 weeks (B), and 8 weeks (C) after injection with anti-Aβ antibodies.
Figure 7:
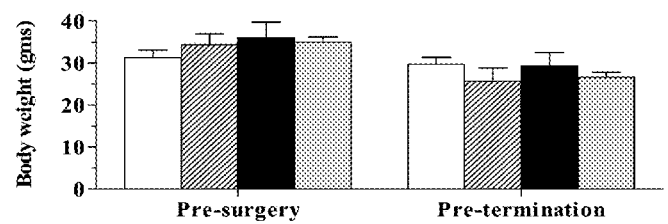
Figure 7:
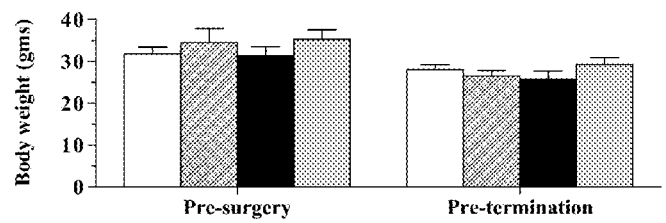

Body weights of mice at various time-points following acute i.c.v. infusion of anti-Aβ $IgG_1$ or its $F(ab')_2$ fragments are shown in FIG. 7. The mean±SEM values for body weights of mice recorded before the surgical administration of experimental article and before the termination procedure have been indicated for all experimental groups. A repeated measures ANOVA revealed a significant effect of time ($F_{1, 11}=18.101$, P=0.001, 1 week post-injection; $F_{1, 9}=20.268$, P=0.001, 4 weeks post-injection; $F_{1, 12}=46.417$, P<0.001, 8 weeks post-injection) but not treatment ($F_{3, 11}=0.781$, P=0.529, 1 week post-injection; $F_{3, 9}=0.33$, P=0.804, 4 weeks post-injection; $F_{3, 12}=0.692$, P=0.574, 8 weeks post-injection) on the body weight of mice maintained for 1 (A), 4 (B) and 8 (C) week/s post-injection.

Figure 8:
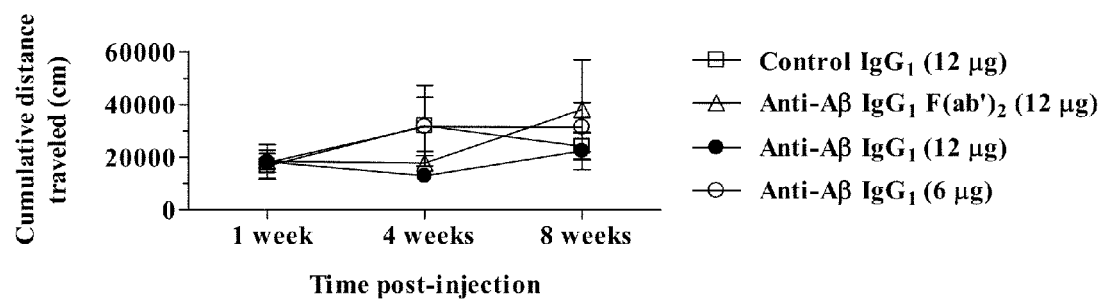
FIG. 8 is a graph of locomotor activity of mice 1, 4 and 8 weeks after injection with anti-Aβ antibodies.

Results of locomotor activity of mice at 1, 4, and 8 weeks after acute i.c.v. infusion of anti-Aβ $IgG_1$ or its $F(ab')_2$ fragments are shown in FIG. 8. The mean±SEM values represent cumulative distance traveled by mice in a novel arena, for 1 hr. A two-way ANOVA failed to reveal any significant effect of time ($F_{2, 32}=1.405$, P=0.26) or treatment ($F_{3, 32}=0.476$, P=0.701) on the locomotor activity of mice.

Figure 9:
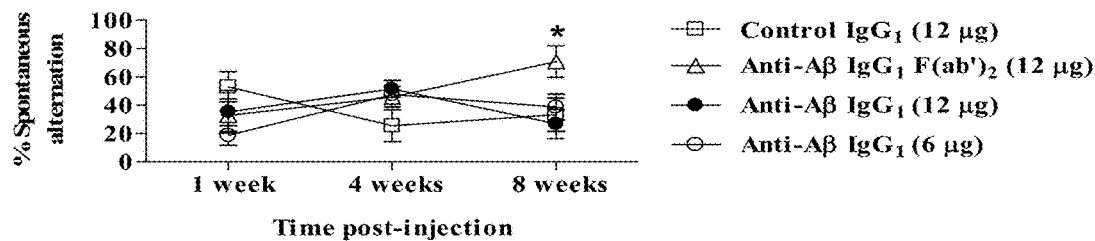
FIG. 9 includes panels A-D of graphs of data obtained from an Y maze alternation assay of mice 1, 4 and 8 weeks after injection with anti-Aβ antibodies.
Figure 9:
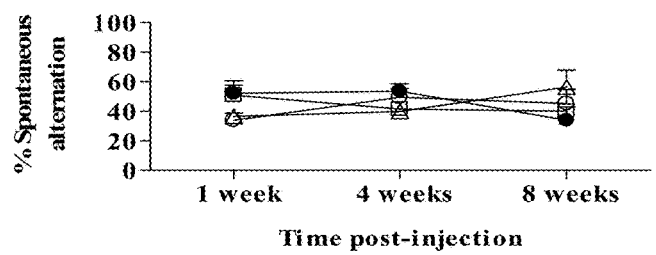
Figure 9:
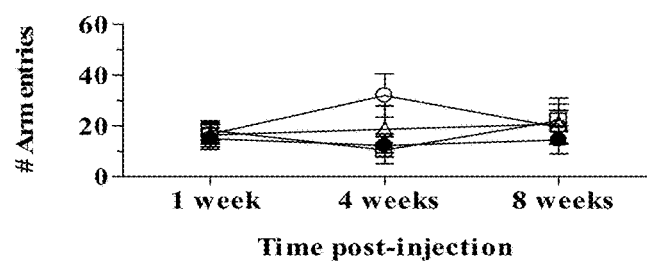
Figure 9:
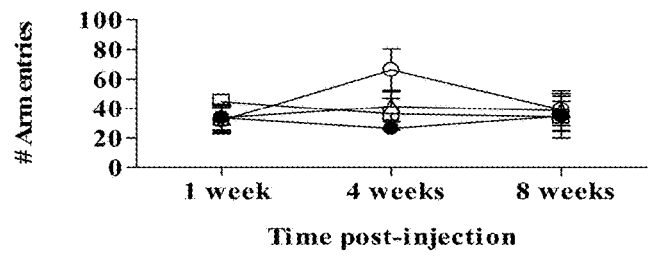

Results of Y-maze alternation task performed by Tg2576 mice at 1, 4, and 8 weeks after acute i.c.v. infusion of anti-Aβ $IgG_1$ or its $F(ab')_2$ fragments are shown in FIG. 9. Percentage spontaneous alternation was scored for mice as follows: (number of performed alternations×100)/number of possible alternations (total number of arm entries—2). (A) Scoring of spontaneous alternation only for the first 5 min of the test revealed a beneficial effect only 8 weeks after injection of anti-Aβ $IgG_1$ $F(ab')_2$ as indicated by mean±SEM values in (A). This effect was not apparent when alterations were scored for 10 min of the test period (B). Recorded mice alterations were independently scored by two individuals, one was blind to the treatments; the inter-scorer Pearson's correlation coefficient was 0.956 (p<0.001). The effects observed in (A) and (B) are independent of any possible changes in the locomotor activity of mice, evident from the lack of differences observed in the number of arm entries exhibited by mice from different treatment groups (C and D). * p<0.05, significantly different from all the other groups for the same post-infusion time point; two-way ANOVA followed by Student Newman Keuls post-hoc test.

Figure 10:
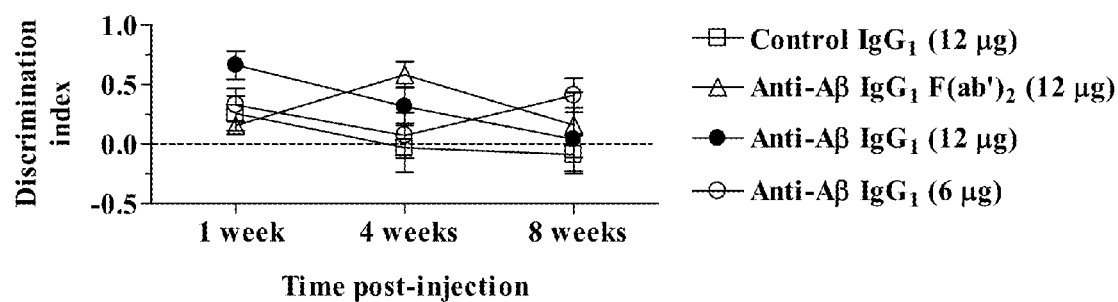
FIG. 10 includes panels A-B of graphs of data obtained from a spatial object location memory assay of mice 1, 4 and 8 weeks after injection with anti-Aβ antibodies.
Figure 10:
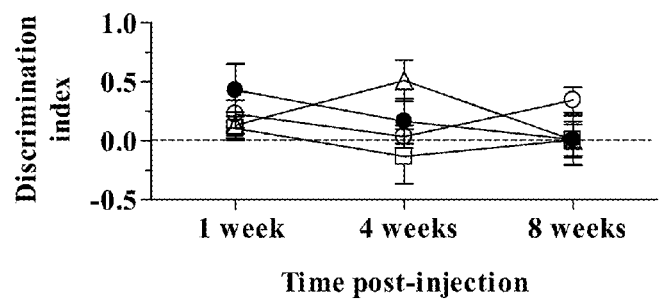

Results of spatial object recognition memory in Tg2576 mice after 1, 4, and 8 weeks of infusing the anti-Aβ $IgG_1$ or its $F(ab')_2$ fragments i.c.v. are shown in FIG. 10. The spatial object recognition memory is represented by a discrimination index, which is calculated as follows: [(Time of exploring the objects whose positions were diagonally switched)−(Time of exploring the objects whose positions were unchanged)]/Time of exploring all objects. (A) The mean±SEM discrimination indices for each treatment group are indicated when scored for only the first 5 min of the test.

A two-way ANOVA failed to demonstrate an effect of time ($F_{2, 32}=1.177$, $P=0.321$) or treatment ($F_{3, 32}=1.425$, $P=0.254$). (B) Similarly, scoring of the entire 10 min test period revealed no significant improvements in the spatial object location memory with any treatments at any time-point post-injection. Two individuals independently scored the recorded mouse behavior. One scorer was blind to the treatment groups; the inter-scorer Pearson's correlation coefficient was 0.981 ($p<0.001$) for this outcome.

The Campbell Switzer and Aβ stains were used to label diffuse and dense, core Aβ plaques in the brains of transgenic mice. The trend for changes in plaque area was similarly detected by both stains, as also indicated by Callahan et al. (2001), *Am. J. Pathol.* 158, 1173-1177. However, the Campbell Switzer stain was much more sensitive than Aβ in detecting plaques. More importantly, the Campbell Switzer stain was able to detect the Aβ plaques in brain parenchyma as well as vasculature, whereas the Aβ stain detected only parenchymal plaques. Ultimately, the slides stained with Campbell Switzer were analyzed for quantifying the % area of cortex and hippocampus that were occupied by parenchymal or vascular plaques (a representative is shown below with scale bar: 100 μm).

Figure 11:
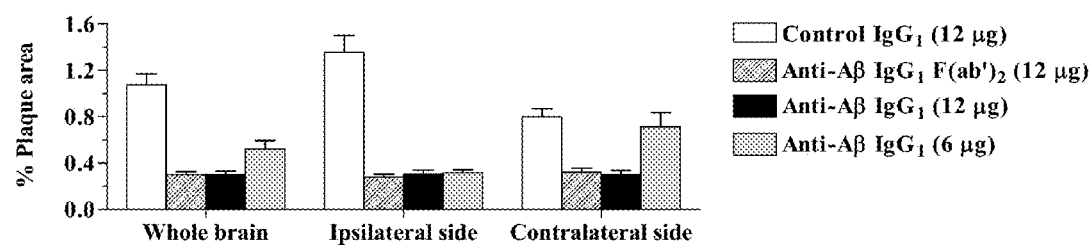
FIG. 11 includes panels A-C of bar graphs of the number of cerebral cortex parenchymal plaques identified in mice one (A), four (B) and eight (C) weeks after injection with anti-Aβ antibodies.
Figure 11:
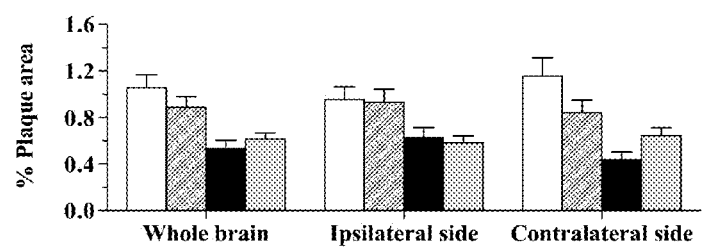
Figure 11:
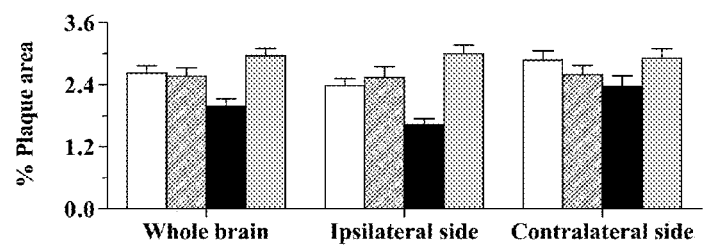

Bilateral changes in the parenchymal Aβ plaque load of Tg2576 mice at 1, 4, and 8 weeks after acute i.c.v. infusion of anti-Aβ $IgG_1$ or its $F(ab')_2$ fragments are shown in FIG. 11. Percentage area of cerebral cortex occupied by parenchymal Aβ plaques was determined by scanning the Campbell Switzer-stained slides at 4× using a bright-field microscope and analyzing scanned images using the Visiopharm system (Visiopharm, Denmark). Treatment-induced changes in parenchymal plaque load were evident in the ipsilateral hemisphere of the brain; these changes also closely paralleled in the contralateral hemisphere of the brain. Bars represent mean±SEM values of the % area of parenchymal plaque in the cortex of the whole brain or ipsilateral vs. contralateral hemispheres of brains from mice maintained for 1 (A), 4 (B), and 8 (C) week/s post-infusion.

Figure 12:
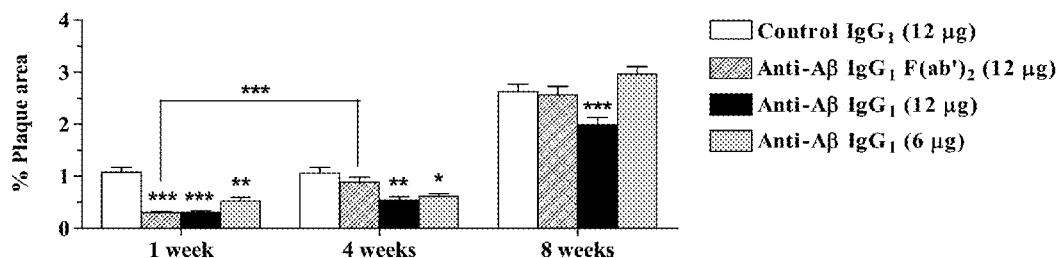
FIG. 12 includes panels A-C of bar graphs of the number of cerebral cortex parenchymal (A), cerebral cortex vascular (B) and hippocampal parenchymal (C) plaques identified in mice 1, 4 and 8 weeks after injection with anti-Aβ antibodies.
Figure 12:
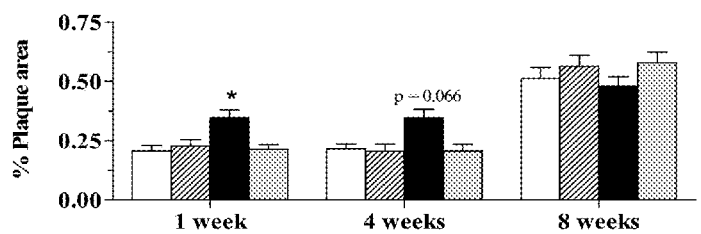
Figure 12:
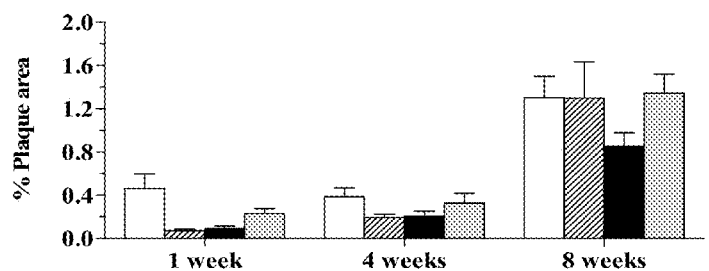

Parenchymal and vascular Aβ plaque load of Tg2576 mice at 1, 4, and 8 weeks after acute i.c.v. infusion of anti-Aβ $IgG_1$ or its $F(ab')_2$ fragments are shown in FIG. 12. The mean±SEM values depict treatment-induced changes in % area of the bilateral cerebral cortex occupied by the parenchymal (A) or vascular (B) Aβ plaques, and % area of the bilateral hippocampus occupied by parenchymal Aβ plaques (C) at 1, 4, and 8 week/s post-infusion. Infusion of anti-Aβ $IgG_1$ $F(ab')_2$ led to a short-term (for only 1 week) decrease in the parenchymal Aβ plaque load, while that of the low-dose (6 μg) anti-Aβ $IgG_1$ reduced the parenchymal plaque load for a longer duration of time (up to 4 weeks) in the cerebral cortex. The high-dose (12 μg) anti-Aβ $IgG_1$ produced a significant decrease in the parenchymal plaque load, but also increased the vascular Aβ. *$p<0.05$, $p<0.01$, *$p<0.001$; significantly different from the corresponding control or as indicated; two-way ANOVA followed by Tukey's post-hoc test. In addition, all treatment groups were significantly different at 8 weeks post-infusion as compared to the same at 1- and 4-weeks post-injection.

Figure 13:
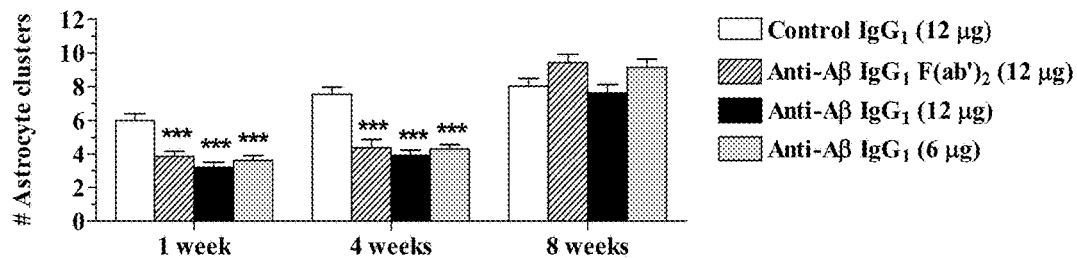
FIG. 13 is a bar graph of astrocyte clusters identified in mice 1, 4 and 8 weeks after injection with anti-Aβ antibodies.

The number of astrocyte clusters observed in Tg2576 mice at 1, 4, and 8 weeks after acute i.c.v. infusion of anti-Aβ $IgG_1$ or its $F(ab')_2$ fragments are shown in FIG. 13. Activated astrocytes were observed to form clusters around dense, core Aβ plaques in the Tg2576 mice, similar to that observed in AD patients (Nicoll et al., 2003). The total number of astrocytic clusters in all GFAP-stained sections was scored separately by two individuals. One individual was blind to the treatment groups; the inter-scorer Pearson's correlation coefficient was 0.925 ($p<0.001$). Bars represent mean±SEM number of GFAP-positive clusters in the coronal sections of mice from each treatment group. ***$p<0.001$; significantly different from the corresponding control; two-way ANOVA followed by Tukey's post-hoc test. In addition, all treatment groups were significantly different at 8 weeks post-injection as compared to the same at 1- and 4-week/s post-injection, except for the control $IgG_1$ group that was significantly different at 1 week post-injection as compared to the same at 4- and 8-weeks.

Figure 14:
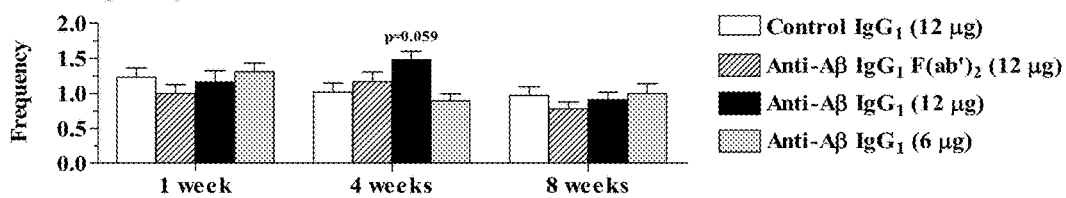
FIG. 14 includes panels A-C of bar graphs of the frequency (A), severity (B) and score (C) of such pathology identified in mice 1, 4 and 8 weeks after injection with anti-Aβ antibodies.
Figure 14:
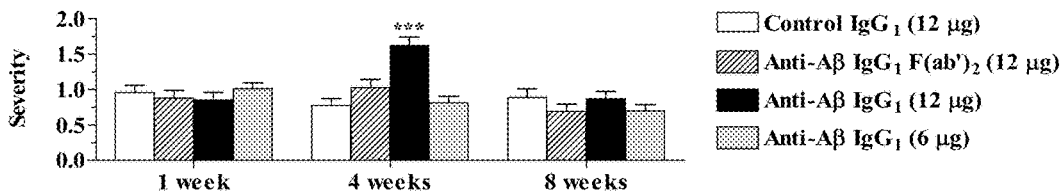
Figure 14:
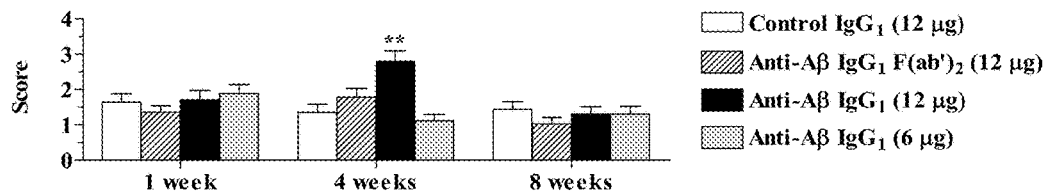

Vascular pathology in Tg2576 mice at 1, 4, and 8 weeks after acute i.c.v. infusion of anti-Aβ $IgG_1$ or its $F(ab')_2$ fragments are shown in FIG. 14. Microhemorrhage events were scored for brain sections as described (Pfeifer et al. (2002), *Science* 298, 1379) in order to determine the (A) Frequency; total number of events per section, (B) Severity; the number of hemosiderin-positive cells per event, classified into four categories of 0 (0 cells), 1 (1-3 cells per event), 2 (4-10 cells per event), 3 (10-20 cells per event), and 4 (>20 cells per event) and (C) Score; frequency×severity of event per section. All Perl's DAB-stained sections were scored separately by two individuals. One individual was blind to the treatment groups; the inter-scorer Pearson's correlation coefficient was 0.804 ($p<0.001$). Bars represent mean±SEM values for each treatment group. $p<0.01$, *$p<0.001$ denote significant difference from the corresponding control. Two-way ANOVA followed by Tukey's post-hoc test was performed for analyzing the frequency scores, while Kruskal-Wallis analyses followed by Dunn's multiple comparison test was performed on the severity and score values. An increase in the frequency, severity and score for vascular pathology was noted only with the anti-Aβ $IgG_1$ (12 μg) treatment 4 weeks post-injection.

Figure 15:
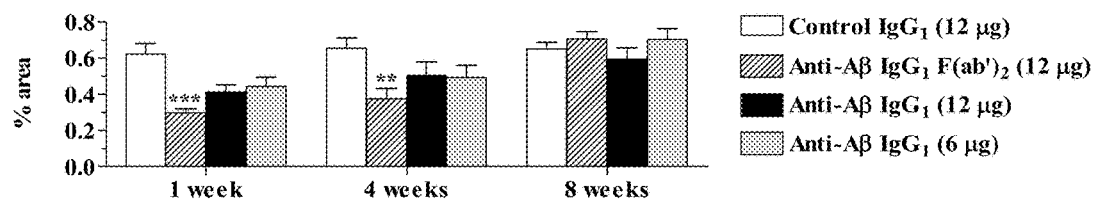
FIG. 15 includes panels A-B of bar graphs of cerebral cortex (A) and hippocampal (B) plaques identified in mice 1, 4 and 8 weeks after injection with anti-Aβ antibodies.
Figure 15:
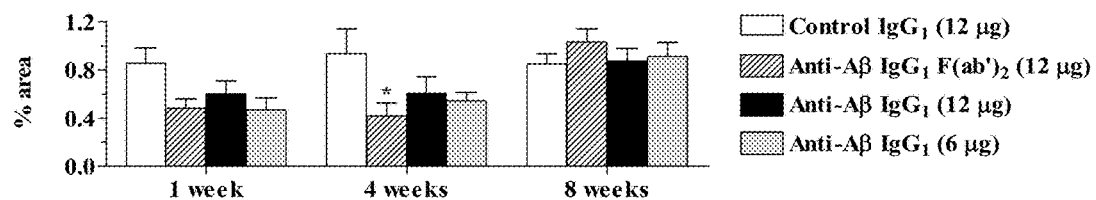

Microglial activation in Tg2576 mice at 1, 4, and 8 weeks after acute i.c.v. infusion of anti-Aβ $IgG_1$ or its $F(ab')_2$ fragments is shown in FIG. 15. The mean±SEM values depict treatment-induced changes in % area of the bilateral (A) cerebral cortex or (B) hippocampus occupied by activated microglia at 1, 4, and 8 weeks post-infusion, as determined by scanning the Ibal-stained slides at 4× using a bright-field microscope and analyzing scanned images using the Visiopharm system. Infusion of anti-Aβ $IgG_1$ $F(ab')_2$ led to a transient (up to 4 weeks) decrease in the activation of microglia, while that of the anti-Aβ $IgG_1$ revealed trends for a transient reduction in microglial activation in both the cerebral cortex and hippocampus. *$p<0.05$, $p<0.01$, *$p<0.001$; significantly different from the corresponding control; two-way ANOVA followed by Tukey's post-hoc test.

3. Summary

An acute unilateral i.c.v. infusion of the anti-Aβ $IgG_1$ or its $F(ab')_2$ fragments was well tolerated by the Tg2576 mice. A dose- and time-dependent, bilateral reduction of parenchymal Aβ plaque loads was achieved with an acute unilateral i.c.v. infusion of the anti-Aβ $IgG_1$ in Tg2576 mice. A relatively transient reduction of parenchymal Aβ plaques was also observed with infusion of the anti-Aβ $IgG_1$-$F(ab')_2$ fragments alone, suggesting a significant role for plaque dissolution in the mechanism by which anti-Aβ $IgG_1$ reduces Aβ plaques. I.c.v. infusions of the anti-Aβ $IgG_1$-$F(ab')_2$ fragments or low dose (6 μg) anti-Aβ $IgG_1$ were devoid of any undesirable effects on vascular Aβ plaques as well as the vascular pathology as observed with high dose (12 μg) anti-Aβ $IgG_1$. Desirable, although short-term, reduction in the inflammatory outcomes of astrogliosis and microgliosis were also noted with treatments of the anti-Aβ $IgG_1$ or its $F(ab')_2$ fragments.

Example 2

Stability Test in Pumps for Chronic Infusion

Before initiating an animal study requiring the implantation of a pump for drug infusion, a pump stability study may be performed to determine if the test molecule or drug is stable in the desired pump. Here, the stability of both 6E10 IgG1 monoclonal antibody the F(ab')2 fragment of the 6E10 IgG1 monoclonal antibody was assessed by ELISA for samples dispensed through the Alzet pump at 37° C. for a duration of 6 weeks.

1. Materials and Methods

Alzet pumps used for this study have reservoir volumes of 200 µL, flow at a rate of 6 µL/Day, and are expected to empty after 6 weeks. 8 Alzet pumps (1-8) were filled with 6E10 $IgG_1$ monoclonal antibody. 8 Alzet pumps (9-16) were filled with the $F(ab')_2$ fragment of the 6E10 $IgG_1$ monoclonal antibody. All pumps were started simultaneously. Samples were pulled weekly from all pumps for the six week duration of the study and stored frozen at −70° C. until testing by ELISA and HPLC. To simulate implanted (body) temperature all pumps were kept in humidity chambers at 37° C. Because the Alzet pumps function by osmotic pressure, each pump was submerged in a 15 mL conical tube containing 0.9% sterile saline. Normal glass vials were used for sample collection.

2. Results

The concentration results for the 6E10 IgG1 monoclonal antibody show an initial drop from T=0 to approximately 63% by week 1 followed by a recovery, ultimately ending at a concentration of approximately 75% at week 6. The initial drop, followed by recovery is suspected to be due to an initial adsorbtion to the catheter. Once enough formulation has passed through the catheter to sufficiently coat the surfaces, the remaining formulation from the reservoir exits the pump with less loss of the antibody.

The concentration results for the F(ab')2 fragment of the 6E10 IgG1 monoclonal antibody show an initial drop from T=0 to approximately 64% by week 1 followed by a recovery, ultimately ending at a concentration of approximately 95% at week 6. As explained above, the initial drop, followed by recovery is suspected to be due to an initial adsorbtion to the catheter. Once enough formulation has passed through the catheter to sufficiently coat the surfaces, the remaining formulation from the reservoir exits the pump with less loss. It may be possibly that due to its smaller size and fewer "sticking sites" more of the F(ab')2 exits the pump.

Both molecules appear stable enough for use in future pump or animal studies. Adsorption loss to the surfaces may be taken into account when determining dose.

Figure 16:
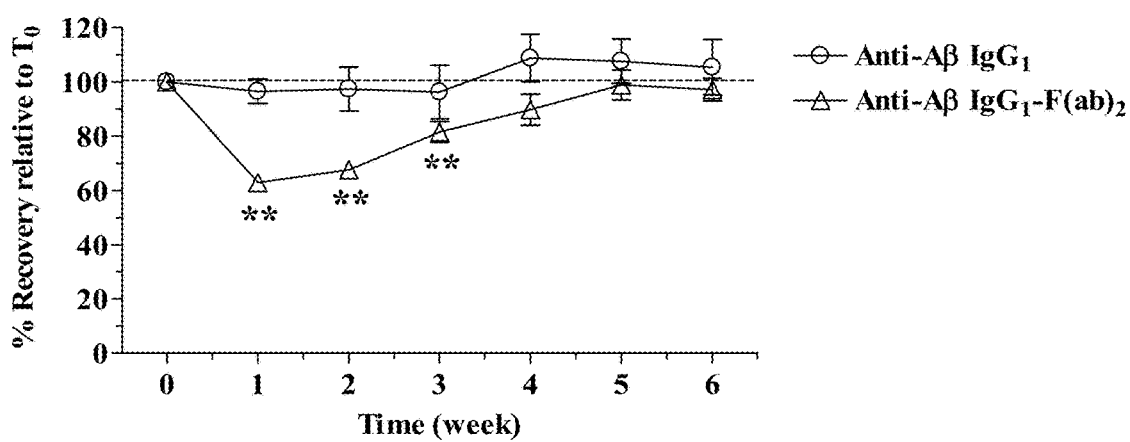
FIG. 16 is a graph of percent recovery of anti-Aβ antibodies every week from Alzet pumps (model 2004) operating in an in vitro system.

Results are shown in FIG. 16 for the Alzet pump. The concentration in the pump samples, obtained over the course of the six week study is shown as percent recovery relative to the naïve (time zero) sample.

Example 3

Stability Test in SynchroMed II (Medtronic, Inc.) Infusion Systems

A study similar to the one presented in Example 2 was performed in the SynchroMed II pump (Medtronic, Inc.) with a catheter suitable for intraventricular or intraparenchymal delivery (a shortened, 50.5 inch, Medtronic Model 8910 catheter). Here, the stability of both 1 mg/ml 6E10 IgG1 monoclonal antibody and 0.1 mg/ml 6E10 IgG1 monoclonal antibody was assessed by ELISA and HPLC for samples dispensed through the SynchroMed infusion system at 37° C. over the course of a 28 day initial pump fill (naïve) cycle followed by a 56 day refill cycle.

An initial loss of antibody to the pump and catheter was observed and was believed to be due to adsorption during the naïve cycle. Loss due to adsorption during the subsequent cycle was negligible. A loss in antibody binding activity was observed. Such a loss was expected because the antibody had been exposed to an elevated temperature (37° C.) for a long period of time. The pH of the formulation remained stable throughout the study and pump performance showed no unexpected deviations from expected performance. In summary, it is appears feasible to use the Synchromed II (Medtronic, Inc.) infusion pump with Medtronic Model 8910 catheter to deliver antibodies directed to Aβ.

Example 4

Chronic Intracerebroventriclar Infusion of Anti-Aβ Antibodies in a Transgenic Mouse Model of Alzheimer's Disease A therapeutically significant reduction of cerebral Aβ was achieved in transgenic AD mouse models upon a single i.c.v. immunization with antibodies targeting the N-terminus of Aβ. Nevertheless, an obvious caveat to the implementation of this protocol was the short-term benefit of Aβ antibodies. Hence, our goal was to determine whether continuous i.c.v. infusion of Aβ antibodies, as opposed to a single administration, would produce a long-lasting therapeutic effect in the transgenic AD mice and to compare the therapeutic efficiency of Aβ antibody when delivered i.c.v. versus the peripheral route.

1. Experimental Design

Mice were split into groups as follows:
1. Tg chronic anti-AD Tg2576 mice receiving chronic i.c.v. infusion of 6E10 (concentration: 1 mg/ml)
2. Tg chronic low dose anti-Aβ Tg2576 mice receiving chronic i.c.v. infusion of 6E10 (concentration: 0.2 mg/ml)
3. Tg chronic control $IgG_1$: Tg2576 mice receiving chronic i.c.v. infusion of control $IgG_1$ (concentration: 1 mg/ml)
4. Tg acute anti-Aβ $IgG_1$: Tg2576 mice receiving acute i.c.v. infusion of 6E10 (0.44 µg/16 µl; produces an acute i.c.v. concentration similar to that achieved with continuous infusion of antibody at concentration: 1 mg/ml)
5. Tg chronic peripheral anti-Aβ $IgG_1$: Tg2576 mice receiving chronic i.p. administration of 6E10 (10 mg/kg dosing; concentration: 1 mg/ml)
6. Tg chronic peripheral control $IgG_1$: Tg2576 mice receiving chronic i.p. administration of control $IgG_1$ (10 mg/kg dosing; concentration: 1 mg/ml)
7. WT chronic anti-Aβ $IgG_1$: WT mice receiving chronic i.c.v. infusion of 6E10 (concentration: 1 mg/ml)
8. WT chronic control $IgG_1$: WT mice receiving chronic i.c.v. infusion of control $IgG_1$ (concentration: 1 mg/ml)
9. WT chronic peripheral anti-Aβ $IgG_1$: WT mice receiving chronic i.p. administration of 6E10 (10 mg/kg dosing; concentration: 1 mg/ml)
10. WT chronic peripheral control $IgG_1$: WT mice receiving chronic i.p. administration of control $IgG_1$ (10 mg/kg dosing; concentration: 1 mg/ml)

Infusion of antibody was performed according to the following schedule:

Day 0: First set of i.p. injections performed.
Day 7: Stereotaxic surgery performed on mice for acute i.c.v. infusion or implantation of the brain infusion cannula connected to the subcutaneously implanted osmotic minipump-catheter tubing assembly.
Second set of i.p. injections performed.
Day 14: Third set of i.p. injections performed.
Day 21: Fourth set of i.p. injections performed.
Day 28: Fifth set of i.p. injections performed.
Day 35: Sixth set of i.p. injections performed.
Day 37: Train for fear conditioning paradigm
Day 38: Test for contextual fear conditioning (20-24 h after training)
Test for cued fear conditioning (4 h after contextual fear testing)
Day 39: Sacrifice the mice for removing the minipump, obtain plasma by direct withdrawal of about 1 ml blood from the mouse's heart for ELISA, and trans-cardial perfusion with saline followed by perfusion with paraformaldehyde (4% in saline) to then extract brain, liver, spleen, and kidney.

Mice receiving chronic i.c.v infusion via an implanted Alzet miniosmotic pump at a rate of 0.25 μl/min, received continuous infusion from day 7 to day 39. The osmotic minipump-catheter assembly was retained for a subsequent 3-day in vitro test of pump functionality.

Male Tg2576 mice and their wild-type littermates (Taconic), aged 17 months, received either saline or anti-Aβ IgG$_1$ antibodies, via either intraperitoneal (i.p.) or i.c.v. infusion as described above. For chronic i.c.v. infusion, the mice received either 200 μg (concentration of antibody infused: 1 mg/ml), or 40 μg (concentration of antibody infused: 0.2 mg/ml). For acute i.c.v. administration, the mice received 0.44 μg antibody (see the Experimental Groups section above). For chronic i.p. administration, the mice received 2000 μg (concentration of injected antibody: 1 mg/ml). The Anti-Ab IgG$_1$ administered was the mouse 6E10 antibody (Covance).

Contextual fear conditioning assay was performed using the five pairing paradigm as described by Dineley et al. (2002, *J. Biol. Chem.*, 277, 22768-22780), and the contextual memory for each mouse was obtained by subtracting the percentage freezing in the novel environment from that in the context.

Brains were processed using MultiBrain® Technology (NeuroScience Associates, Knoxville, Tenn.), and coronally sectioned at 35 μm thickness. A series of 18-20 sections equally spaced at 350 μm intervals across the entire cerebrum were used for each stain. Accordingly, analysis for the cerebral cortex involved 18-20 observations per hemisphere per animal, and for the hippocampus involved 7-9 observations per hemisphere per animal, with 8 animals per treatment group.

The Campbell-Switzer stain was employed to visualize amyloid plaques in the parenchyma and CAA, and confirmed with immunostaining using an Aβ antibody and Congo red (M. J. Callahan et al., *Am. J. Pathol.* 158, 1173 (2001)). The DAB-enhanced Perl's hemosiderin and aminocupric silver stains enabled analyses of cerebral hemorrhages and dystrophic neurites, respectively (M. Pfeifer et al., *Science* 298, 1379 (2002); D. M. Holtzman et al., *Proc. Natl. Acad. Sci. U.S.A.* 97, 2892 (2000)). Astrocytosis and microglial activation around amyloid plaques were evident with immunohistochemical detection of glial fibrillary acidic protein and ionized calcium-binding adaptor molecule 1, respectively. Immunohistochemical detection of mouse IgG and counterstaining with Congo red was performed as previously described (D. M. Wilcock et al., *J. Neurosci.* 24, 6144 (2004)), to reveal the plaque-binding ability of anti-Aβ IgG$_1$ administered in vivo. The Visiopharm Integrator System 2.7 (Visiopharm, Horsholm, Denmark) was used for analysing images of brain sections in order to quantify the percent area of cerebral cortex or hippocampus occupied by the stain depicting parenchymal plaques, CAA, dystrophic neurites, or activated microglia. Two individuals scored the astrocytic reaction surrounding amyloid plaques as well as cerebral hemorrhages. Quantification of cerebral hemorrhages was performed as previously described (M. Pfeifer et al., *Science* 298, 1379 (2002)), with a minor modification in that the mean hemorrhage frequency per section was multiplied with hemorrhage severity to generate the overall hemorrhage score.

Plasma levels of Aβ were assayed using the BetaMark x-40 ELISA kit (Covance). For the anti-Aβ IgG$_1$ ELISA, the antibody was captured using the Aβ$_{1-40}$ peptide (Covance) and detected using HRP-labeled, Fc-specific anti-mouse IgG (Jackson ImmunoResearch, West Grove, Pa.).

All analyses were performed blind. An average score was used when two individuals scored the behavioral or histological outcomes; the inter-scorer reliability ranged from 0.801-0.972 ($P<0.0001$). Data are expressed as mean±SEM. Statistical analyses were performed with GraphPad Prism 4.0 (GraphPad Software, San Diego, Calif.) using a two-tailed t test, a one-way ANOVA followed by Tukey's post-hoc test or Kruskal-Wallis analysis followed by Dunn's multiple-comparison test, as appropriate.

2. Results

Figure 17:
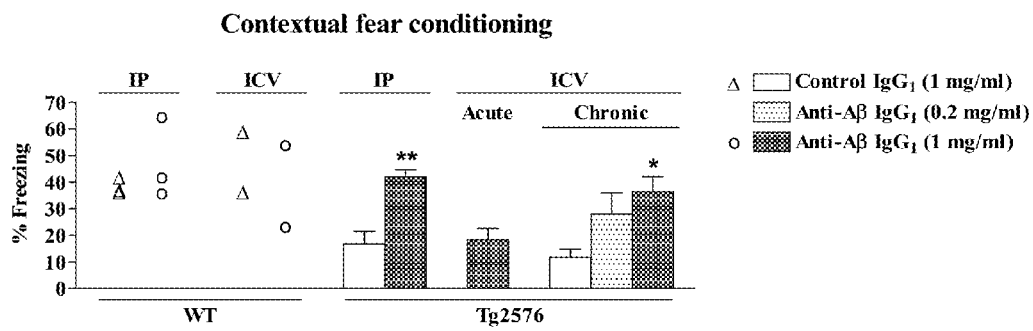
FIG. 17 is a graph of percent freezing in a conditioned fear avoidance assay in mice receiving peripheral and central administration of anti-Aβ antibodies.

Results of the contextual fear conditioning assay are shown in FIG. 17. The control IgG1-treated transgenic mice demonstrated a pronounced reduction in freezing behavior relative to the control IgG1-treated wildtype mice. No difference in freezing was observed between wild-type mice receiving high dose Aβ IgG1 and wild-type mice receiving the control IgG1. In contrast, improvement (increased freezing) was seen in transgenic mice receiving 1 mg/ml Aβ IgG1 peripherally or i.c.v. (relative to control IgG1). Further, the improvement rendered the transgenic mice indistinguishable from the wild-type mice. For i.c.v. administration, the effect was dose dependent.

Figure 18:
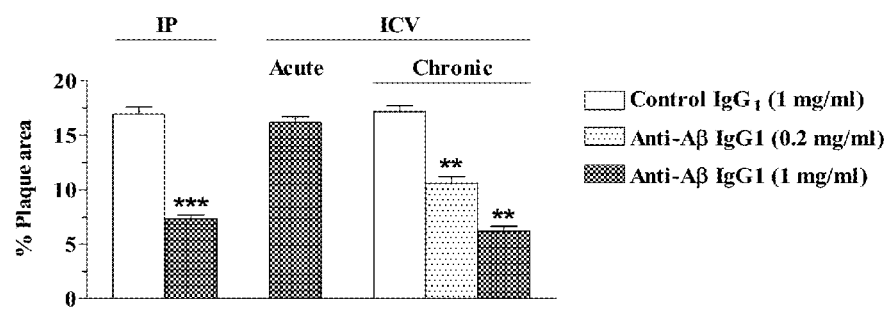
FIG. 18 includes panels A-B of bar graphs of parenchymal (A) and vascular (B) plaques identified in the cerebral cortex of mice receiving peripheral and central administration of anti-Aβ antibodies.
Figure 18:
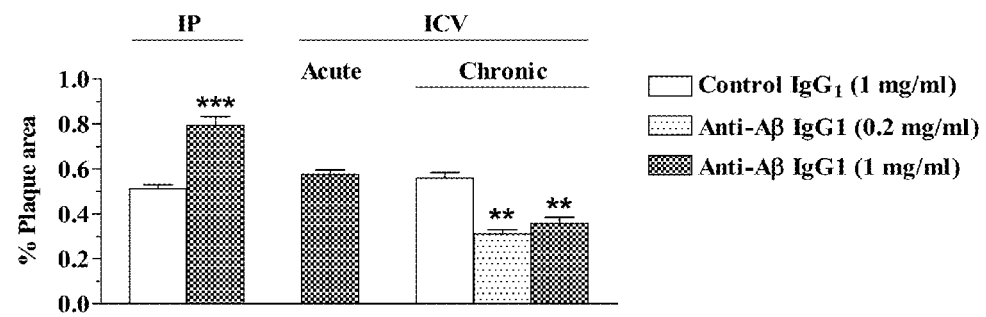
Figure 19:
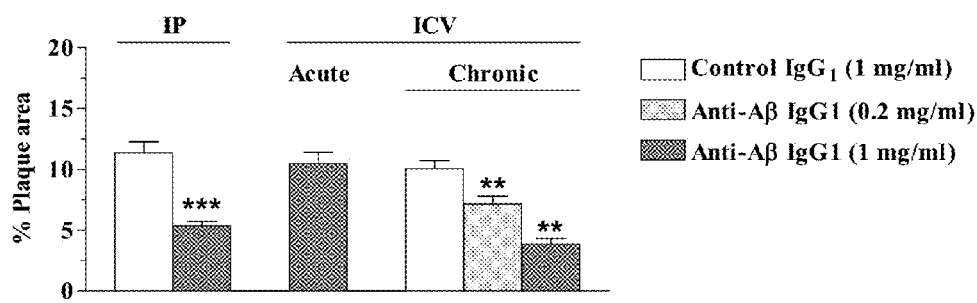
FIG. 19 includes panels A-B of bar graphs of parenchymal (A) and vascular (B) plaques identified in the hippocampus of mice receiving peripheral and central administration of anti-Aβ antibodies.
Figure 19:
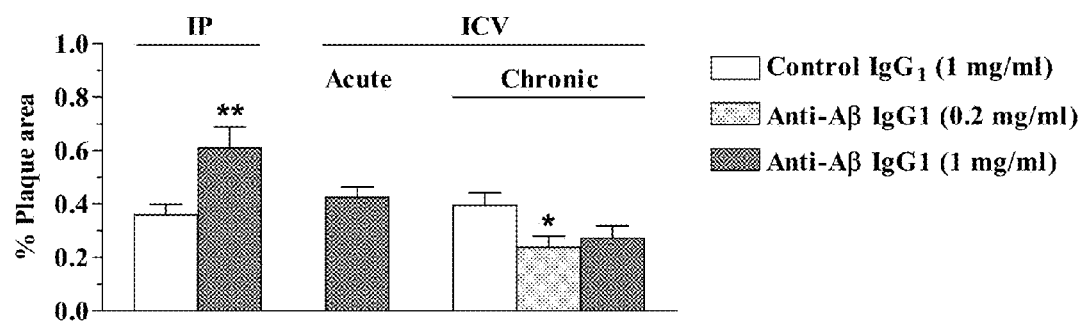
Figure 20:
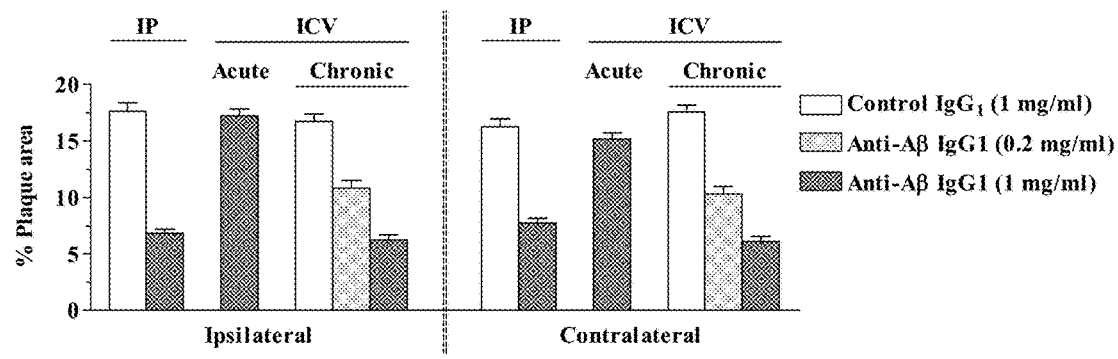
FIG. 20 includes panels A-B of bar graphs of parenchymal (A) and vascular (B) plaques identified in the each hemisphere of the cerebral cortex of mice receiving peripheral and central administration of anti-Aβ antibodies.
Figure 20:
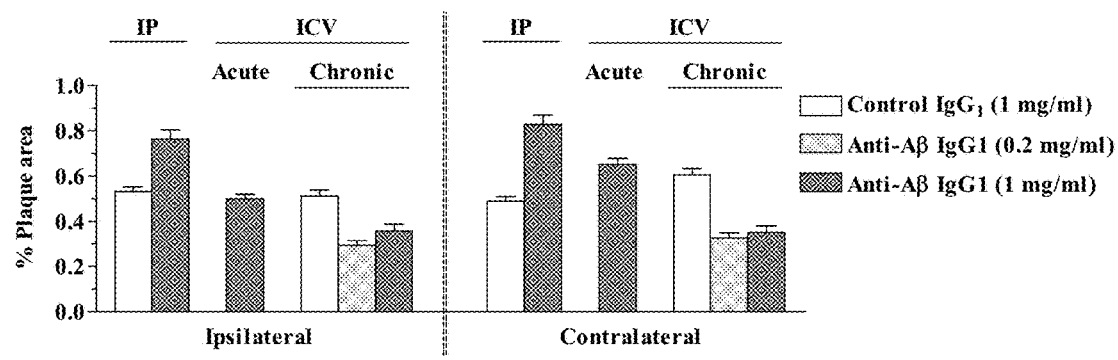
Figure 21:
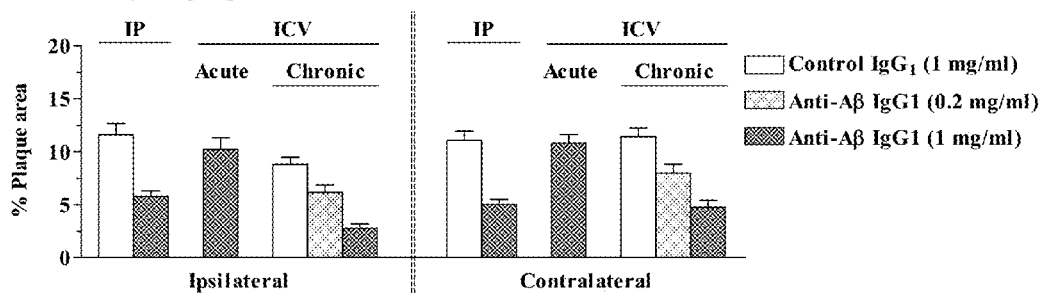
FIG. 21 includes panels A-B of bar graphs of parenchymal (A) and vascular (B) plaques identified in the each hemisphere of the hippocampus of mice receiving peripheral and central administration of anti-Aβ antibodies
Figure 21:
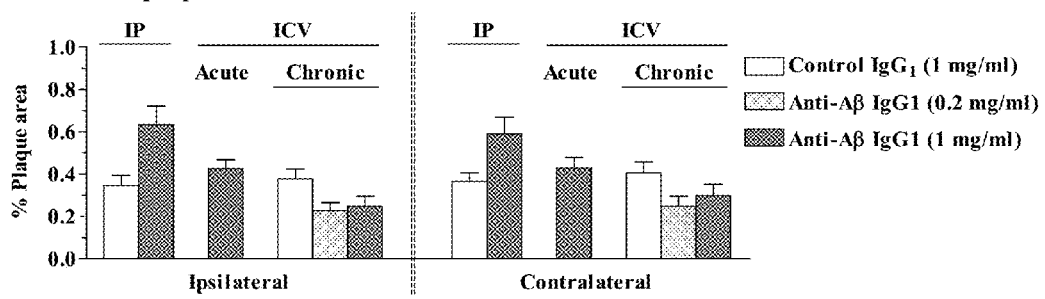

As shown in FIG. 18A, both peripheral and i.c.v. administration of Aβ IgG1 resulted in a lower number of parenchymal plaques compared to transgenic mice receiving control IgG1 in the cerebral cortex. For i.c.v. administration, the effect was dose-dependent. Referring to FIG. 18B, peripheral administration of Aβ IgG1 resulted an increased number of cerebral vascular plaques compared to transgenic mice receiving control IgG1 intraparitoneally (i.p.) in the cerebral cortex. In contrast, mice receiving either low dose (0.2 mg/ml) or high dose (1 mg/ml) i.c.v. administration of Aβ IgG1 had a reduced number of vascular plaques compared to transgenic mice receiving i.c.v. control IgG1. Similar trends were seen for parenchymal and vascular plaques in the hippocampus (FIG. 19). Data from ipsalateral and contralateral (relative to site of infusion) sides of the brain followed the same trends in both the cerebral cortex (FIG. 20) and the hippocampus (FIG. 21) with regard to parenchymal and vascular plaques.

Figure 22:
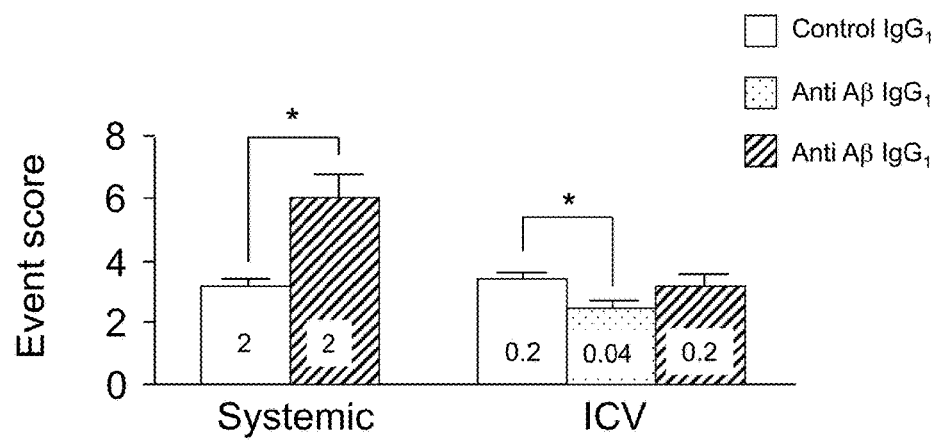
FIG. 22 is a bar graph of cerebral hemorrhages identified in brains of mice receiving a control $IgG_1$ or an Aβ: anti-Aβ $IgG_1$.

As shown in FIG. 22, cerebral hemorrhages increased upon systemic administration of anti-Aβ IgG$_1$, but were unchanged and reduced with i.c.v administrations of 0.2 and 0.04 mg anti-Aβ IgG$_1$, respectively. Antibody-stimulated 1) recruitment of microglia around plaques or 2) perivascular efflux of cerebral Aβ are potential mechanisms for increases in CAA and associated vascular leakage (D. Morgan, *Neurodegener. Dis.* 2, 261 (2005)).

Figure 23:
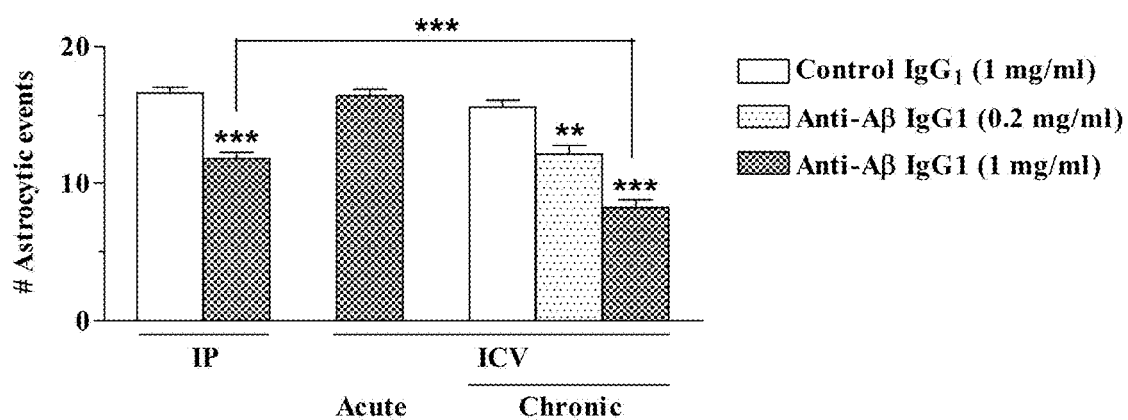
FIG. 23 is a bar graph of astrocytosis events identified surrounding plaques in brains of mice receiving a control $IgG_1$ or an Aβ: anti-Aβ $IgG_1$.
Figure 24:
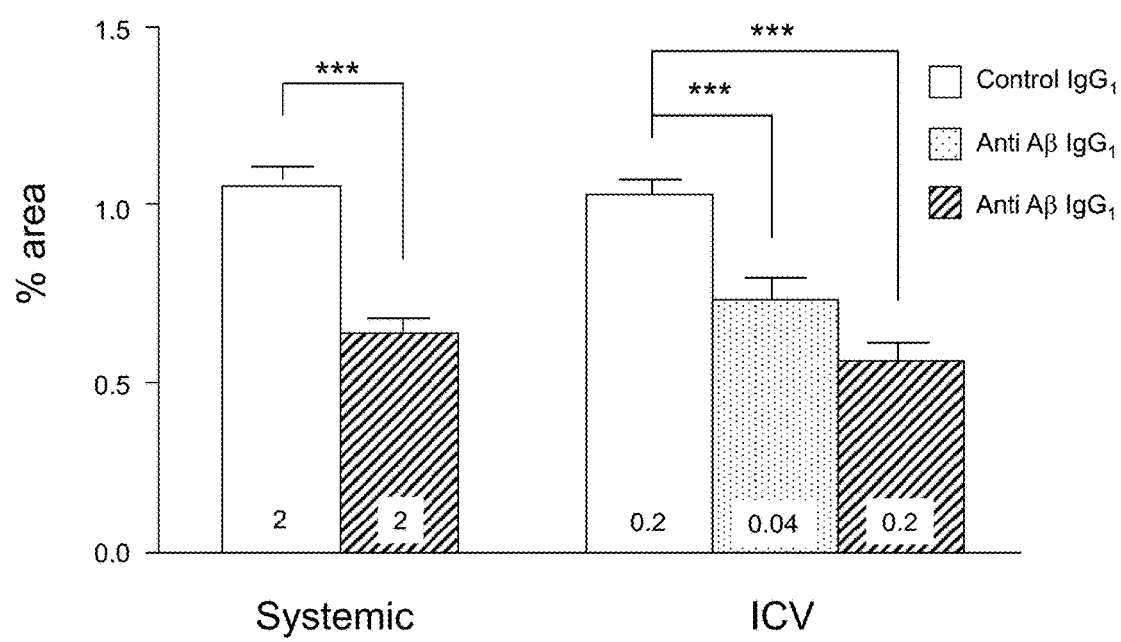
FIG. 24 includes panels A-E of bar graphs of percentage of the area of cerebral cortex and hippocampus (A), total cerebral cortex (B), total hippocampus (C), ipsalateral and contralateral cerebral cortex (D) and ipsalateral and contralateral hippocampus (E) within the brains of mice in which dystrophic neurites were identified in mice receiving a control $IgG_1$ or an Aβ: anti-Aβ $IgG_1$.
Figure 24:
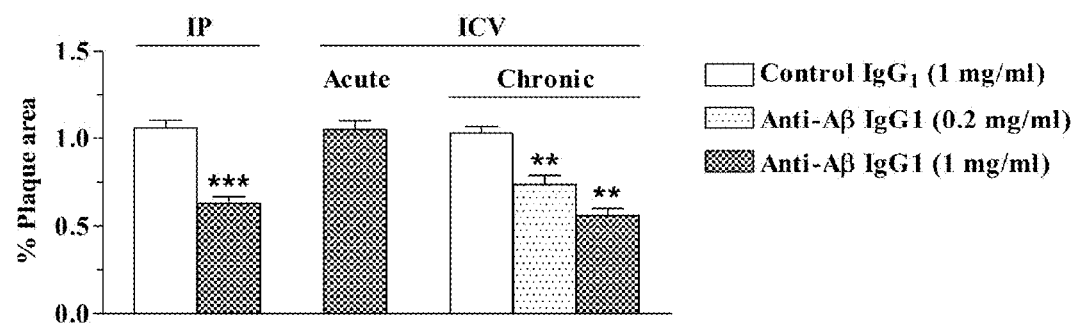
Figure 24:
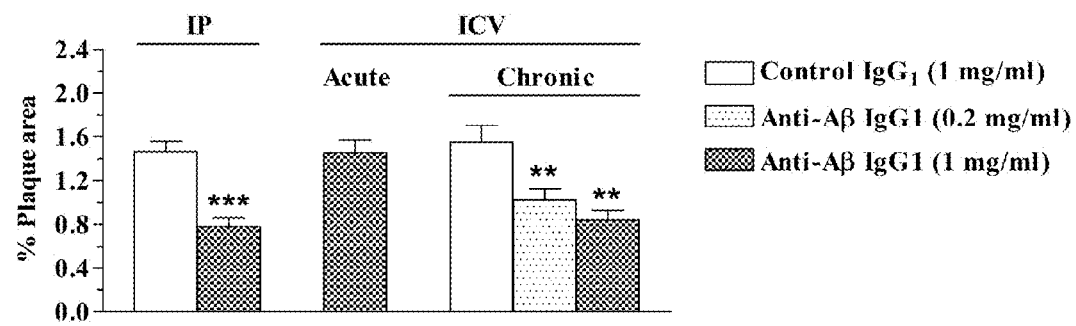
Figure 24:
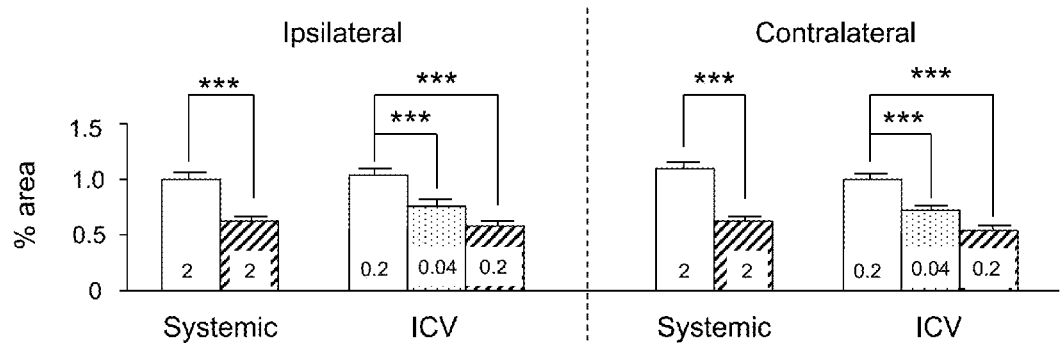
Figure 24:
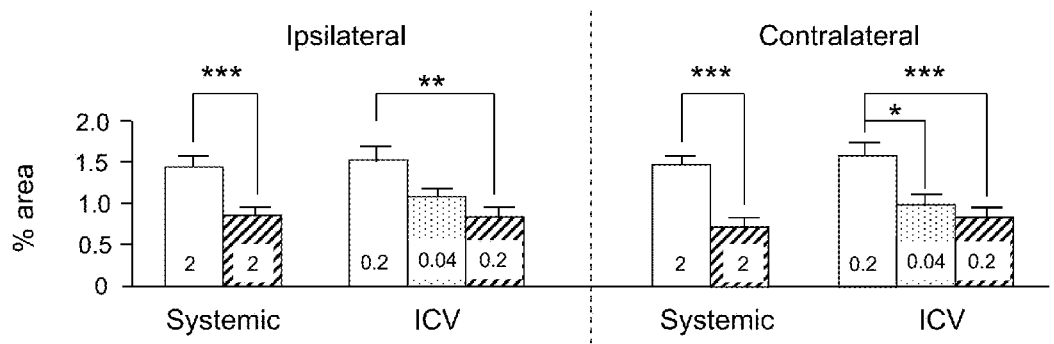
Figure 25:
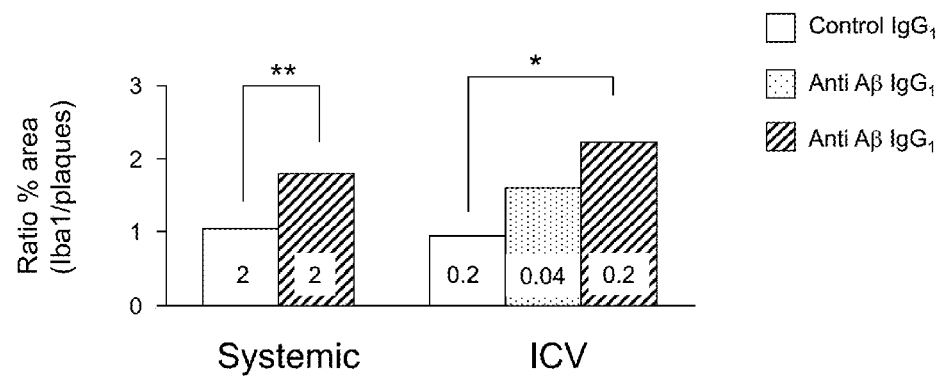
FIG. 25 includes panels A-C of bar graphs of microglial activation (ratio of percent cortical area occupied by activated microglia to the area occupied by plaques) in cerebral cortex and hippocampus (A), cerebral cortex (B) and hippocampus (C) of brains of mice receiving a control $IgG_1$ or an Aβ: anti-Aβ $IgG_1$.
Figure 25:
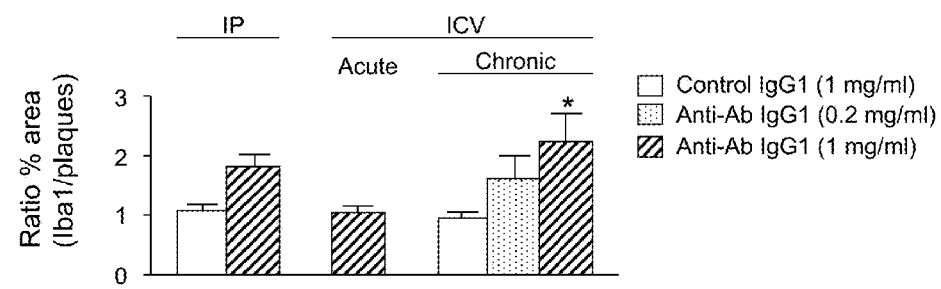
Figure 25:
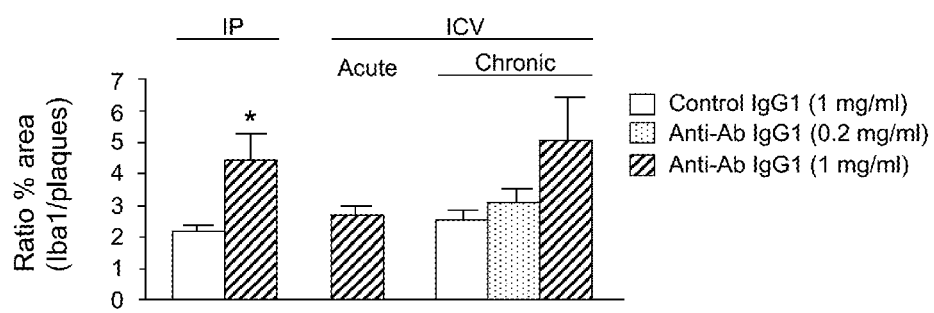
Figure 26:
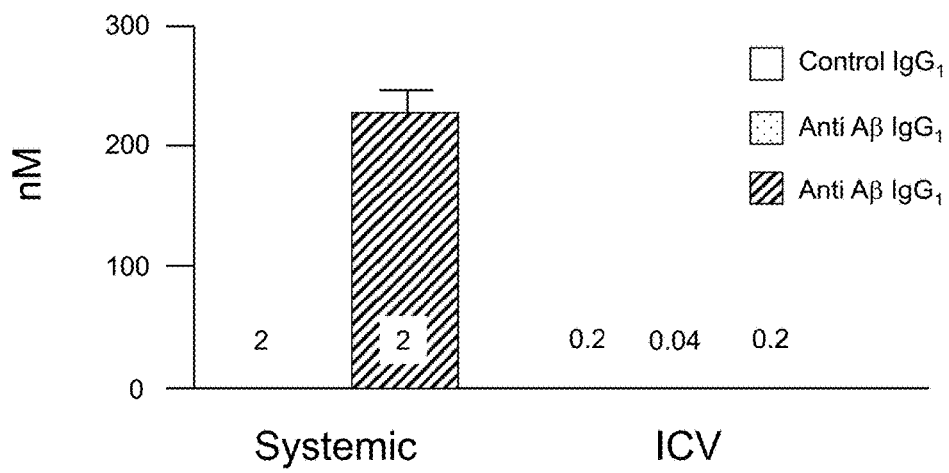
FIG. 26 is a bar graph of plasma concentration of Aβ in mice receiving a control $IgG_1$ or an Aβ: anti-Aβ $IgG_1$.

The astrocytic inflammatory response to amyloid plaques (FIG. 23) and neuritic dystrophy (FIGS. 24A-E) significantly declined after systemic or i.c.v anti-Aβ IgG$_1$ treatment of the Tg2576 mice. Association of anti-Aβ IgG$_1$ with plaques was observed (data not shown) and is indicative of the parenchymal penetration of antibody upon systemic as well as i.c.v. administrations. Subsequently, both systemic and i.c.v. anti-Aβ IgG$_1$ produced a significant activation of microglia surrounding the deposited amyloid (FIGS. 25A-C), which was calculated by the ratio of percent cortical area occupied by activated microglia to the area occupied by plaques. However, plasma Aβ was elevated after systemic but not i.c.v. treatment with anti-Aβ IgG$_1$ (FIG. 26), supporting the notion that perivascular clearance of cerebral Aβ may enhance the susceptibility to CAA and microhemorrhages following systemic delivery of anti-Aβ IgG$_1$.

Figure 27:
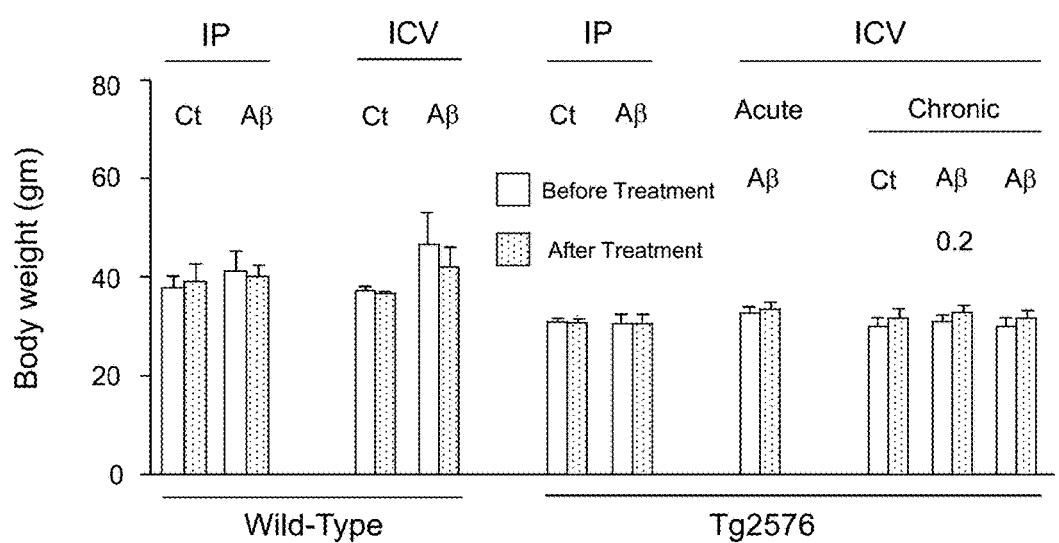
FIG. 27 is a bar graph of body weights of mice before and after treatment with a control $IgG_1$ or an Aβ: anti-Aβ $IgG_1$. Ct: Control $IgG_1$; Aβ: anti-Aβ $IgG_1$; IP: Systemic delivery; ICV: ICV delivery, 1 mg/ml concentration for all treatments, except for the group denoted "0.2", where the delivered concentration was 0.2 mg/ml.
Figure 28:
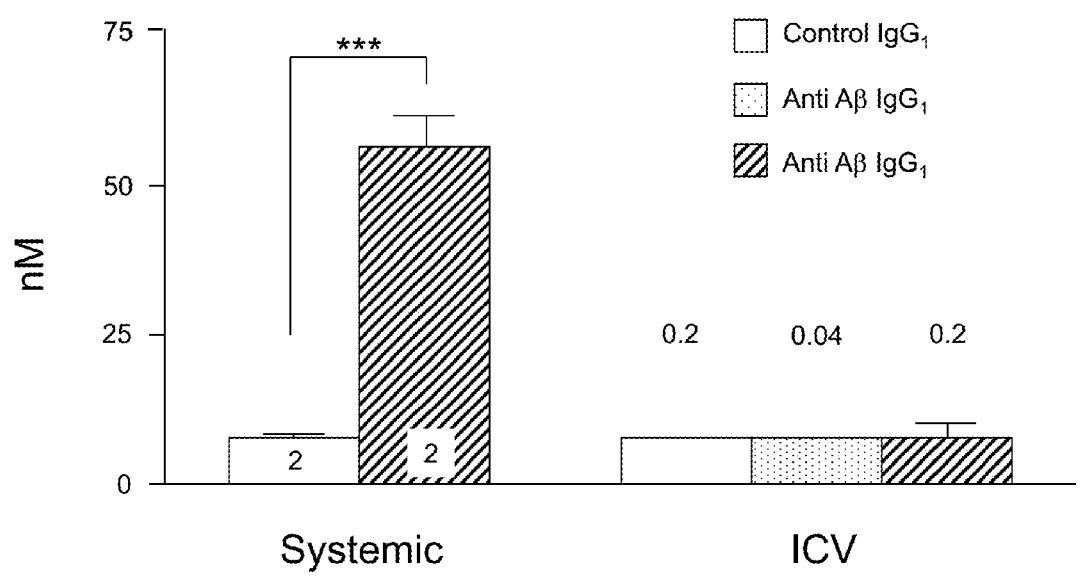
FIG. 28 is a bar graph of plasma concentration of anti-Aβ antibody in mice receiving a control $IgG_1$ or an Aβ: anti-Aβ $IgG_1$.

With reference to FIG. 27, none of the treatments changed the body weight of mice. In addition, sections across the liver, spleen and kidneys were stained for H&E and analyzed by a pathologist that was blind to the treatment groups (data not shown). None of the treatments produced any significant morphological alterations in the analyzed tissue. Antibody binding to amyloid plaques was evident after systemic as well as i.c.v. administrations of anti-Aβ but not control IgG$_1$, as revealed by HRP immunohistochemical product for mouse IgG counterstained with Congo red (not shown). In addition, and as shown in FIG. 28, anti-Aβ IgG$_1$ was not detectable in plasma following i.c.v. administration.

3. Conclusion

Prolonged icy infusion of anti-Aβ IgG$_1$ effectively alleviates the behavioral and pathological impairments in the Tg2576 mouse model of AD. More importantly, i.c.v. delivery of anti-Aβ IgG$_1$ provides an unexpected opportunity to reduce CAA and associated microhemorrhages, which present a significant concern in the clinical testing of systemic immunotherapy (R. L. Patton et al., *Am. J. Pathol.* 169, 1048 (2006); D. Morgan, *Neurodegener. Dis.* 2, 261 (2005); V. Vasilevko, D. H. Cribbs, *Neurochem. Int.* 49, 113 (2006).

Given its efficacy at substantially lower doses, i.c.v.-targeted passive immunotherapy, regardless of the antibody or antigen, may offer a pragmatic approach for the long-term management of neurodegenerative disorders. For example, i.c.v.-targeted passive immunotherapy may be useful for treating diseases such as AD, prion and Parkinson's disease.

Thus, embodiments of METHODS AND DEVICE TO NEUTRALIZE SOLUBLE TOXIC AGENTS IN THE BRAIN are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method for clearing cerebral vascular amyloid plaques in a subject in need thereof, comprising:
   chronically delivering to a cerebral ventricle of the subject an anti-Aβ antibody in an amount effective to clear the cerebral vascular amyloid plaques,
   wherein the anti-Aβ antibody is chronically delivered to the subject's cerebral ventricle from a reservoir of an implantable infusion device.

2. The method of claim 1, wherein the antibody binds Aβ42.

3. The method of claim 1, wherein the antibody binds Aβ40.

4. The method of claim 1, wherein the antibody binds an intracellular Aβ3.

5. The method of claim 1, wherein the antibody comprises an immunoglobulin domain.

6. The method of claim 1, wherein the antibody is a F(ab')2 fragment.

7. A method for treating a subject having a cerebral vascular disease associated with increased or aberrant soluble amyloid beta (Aβ), amyloid fibrils, or amyloid plaques, wherein the disease is selected from the group consisting of Lewy body dementia and Down's syndrome, the method comprising:
   chronically delivering to a cerebral ventricle of the subject an anti-Aβ antibody in an amount effective to treat the disease and to clear cerebral vascular amyloid plaques in the subject,
   wherein the anti-Aβ antibody is chronically delivered to the subject's cerebral ventricle from a reservoir of an implantable infusion device.

8. The method of claim 7, wherein chronically delivering the antibody comprises delivering a composition comprising the antibody for a month or longer.

9. The method of claim 8, wherein delivering the antibody for a month or longer comprises delivering the composition comprising the antibody continuously for a month or longer.

10. The method of claim 9, wherein delivering the antibody continuously comprises delivering pulsed boluses of the composition comprising the antibody.

11. A method for treating Alzheimer's disease and clearing cerebral vascular amyloid plaques in a subject in need thereof, comprising:
   chronically delivering to a cerebral ventricle of the subject an anti-Aβ antibody in an amount effective to treat the Alzheimer's disease and clear the cerebral vascular amyloid plaques,
   wherein the anti-Aβ antibody is chronically delivered to the subject's cerebral ventricle from a reservoir of an implantable infusion device.

12. The method of claim 11, wherein the antibody binds Aβ42.

13. The method of claim 11, wherein the antibody binds Aβ40.

14. The method of claim 11, wherein the antibody binds an intracellular Aβ.

15. The method of claim 11, wherein the antibody comprises an immunoglobulin domain.

16. The method of claim 11, wherein the antibody is a F(ab')2 fragment.

17. The method of claim 11, further comprising introducing a composition comprising the antibody to the reservoir.

18. The method of claim 11, wherein chronically delivering the antibody comprises delivering a composition comprising the antibody for a month or longer.

19. The method of claim 18, wherein delivering the antibody for a month or longer comprises delivering the composition comprising the antibody continuously for a month or longer.

20. The method of claim 19, wherein delivering the antibody continuously comprises delivering pulsed boluses of the composition comprising the antibody.

* * * * *

UNITED STATES PATENT AND TRADEMARK OFFICE
CERTIFICATE OF CORRECTION

PATENT NO. : 9,580,494 B2
APPLICATION NO. : 14/719795
DATED : February 28, 2017
INVENTOR(S) : Shafer et al.

It is certified that error appears in the above-identified patent and that said Letters Patent is hereby corrected as shown below:

In the Claims

Column 30, Line 6: "antibody binds an intracellular Aβ3" should read --antibody binds an intracellular Aβ--

Signed and Sealed this
Twenty-fourth Day of July, 2018

Andrei Iancu
*Director of the United States Patent and Trademark Office*